United States Patent
Wen et al.

(10) Patent No.: US 10,416,171 B2
(45) Date of Patent: Sep. 17, 2019

(54) INFLUENZA POTENCY ASSAYS

(71) Applicant: Seqirus UK Limited, Berkshire (GB)

(72) Inventors: Yingxia Wen, Cambridge, MA (US); Ethan Settembre, Cambridge, MA (US); Zihao Wang, Cambridge, MA (US)

(73) Assignee: Seqirus UK Limited, Berkshire (GB)

( * ) Notice: Subject to any disclaimer, the term of this patent is extended or adjusted under 35 U.S.C. 154(b) by 0 days.

(21) Appl. No.: 15/741,816

(22) PCT Filed: Jul. 7, 2016

(86) PCT No.: PCT/EP2016/066200
§ 371 (c)(1),
(2) Date: Jan. 4, 2018

(87) PCT Pub. No.: WO2017/005880
PCT Pub. Date: Jan. 12, 2017

(65) Prior Publication Data
US 2018/0196061 A1  Jul. 12, 2018

(30) Foreign Application Priority Data

Jul. 7, 2015 (EP) .................................. 15175765.5
Jan. 26, 2016 (EP) .................................. 16152829.4

(51) Int. Cl.
*G01N 33/68* (2006.01)
*A61K 39/145* (2006.01)
*C12N 7/00* (2006.01)
*G01N 33/569* (2006.01)

(52) U.S. Cl.
CPC ....... *G01N 33/6848* (2013.01); *A61K 39/145* (2013.01); *C12N 7/00* (2013.01); *G01N 33/56983* (2013.01); *C12N 2760/16034* (2013.01); *C12N 2760/16051* (2013.01); *G01N 2333/11* (2013.01)

(58) Field of Classification Search
CPC ......... G01N 33/6848; G01N 33/56983; G01N 2333/11; A61K 39/145; C12N 7/00; C12N 2760/16051; C12N 2760/16034
See application file for complete search history.

(56) References Cited

U.S. PATENT DOCUMENTS 5,858,368 A    1/1999 Smith et al.
2011/0201039 A1* 8/2011 Barr .................... G01N 30/7233
                                                           435/23

FOREIGN PATENT DOCUMENTS

WO    WO 2009/110873 A2    9/2009
WO    WO 2010/136896 A1    12/2010

OTHER PUBLICATIONS

Williams TL, Luna L, Guo Z, Cox NJ, Pirkle JL, Donis RO, Barr JR. Quantification of influenza virus hemagglutinins in complex mixtures using isotope dilution tandem mass spectrometry. Vaccine. May 12, 2008;26(20):2510-20.*
Böttcher E, Matrosovich T, Beyerle M, Klenk HD, Garten W, Matrosovich M. Proteolytic activation of influenza viruses by serine proteases TMPRSS2 and HAT from human airway epithelium. J Virol. Oct. 2006;80(19):9896-8.*
Lazarowitz SG, Choppin PW. Enhancement of the infectivity of influenza A and B viruses by proteolytic cleavage of the hemagglutinin polypeptide. Virology. Dec. 1975;68(2):440-54.*
Orlich M, Linder D, Rott R. Trypsin-resistant protease activation mutants of an influenza virus. J Gen Virol. Mar. 1995;76 ( Pt 3):625-33.*
"Protein Precipitation". http://www.ucdenver.edu/academics/colleges/Graduate-School/academic-programs/biomol/program/strucbiocores/massspec/Documents/Protein%20precipitation.pdf. May 9, 2014.*
Ceriotti et al., "Trimer formation determines the rate of influenza virus haemagglutinin transport in the early stages of secretion in Xenopus oocytes," J Cell Biol, 111(2):409-420, (1990).
Kang, "Development of LC-MS method for quantification of haemagglutinin in influenza vaccine," FEBS Journal, 281(Suppl. 1):113, (2014).
Wei et al., "Comparative efficacy of neutralizing antibodies elicited by recombinant hemagglutinin proteins from avian H5N1 influenza virus," J Virol, 82(13):6200-6208, (2008).
Wen et al., "Conformationally selective biophysical assay for influenza vaccine potency determination," Vaccine, 33(41):5342-5349, (2015).
Wen et al., "Trypsin pre-treatment corrects SRID over-estimation of immunologically active, pre-fusion HA caused by mixed immunoprecipitin rings," Vaccine, 34(29):3388-3395, (2016).
International Search Report of International Application No. PCT/EP2016/066200, dated Aug. 17, 2016.
Written Opinion of the International Searching Authority for International Application No. PCT/EP2016/066200.
Picotti et al., "Selected reaction monitoring-based proteomics: workflows, potential, pitfalls and future directions," Nat Methods, 9(6):555-566, (2012).
Skehel et al., "Changes in the conformation of influenza virus hemagglutinin at the pH optimum of virus-mediated membrane fusion," Proc Natl Acad Sci U S A, 79(4):968-972, (1982).
Thompson et al., "Analytical technologies for influenza virus-like particle candidate vaccines: challenges and emerging approaches," Virol J, 10:141, (2013).

* cited by examiner

*Primary Examiner* — Rachel B Gill
(74) *Attorney, Agent, or Firm* — Finnegan, Henderson, Farabow, Garrett & Dunner, LLP

(57) ABSTRACT

The present application discloses stability-indicating potency assays for influenza vaccines.

26 Claims, 17 Drawing Sheets
Specification includes a Sequence Listing.

Figure 1
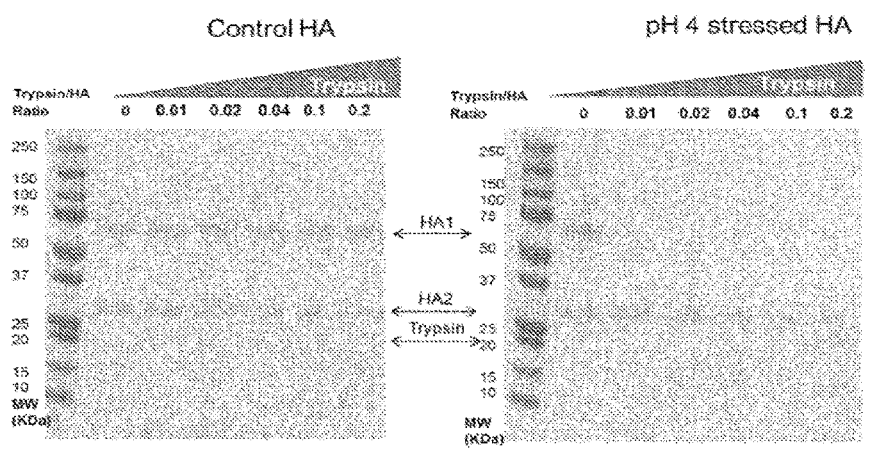
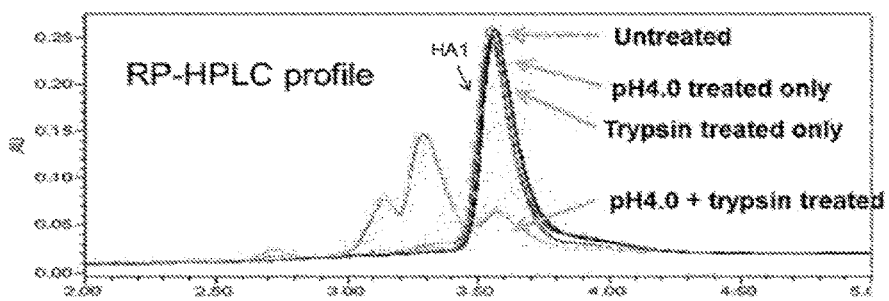

Figure 3
A
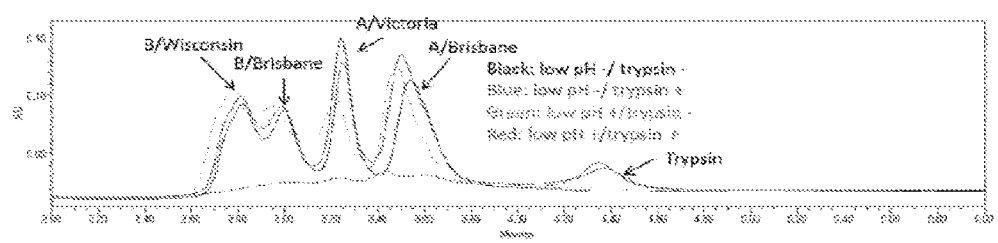
B
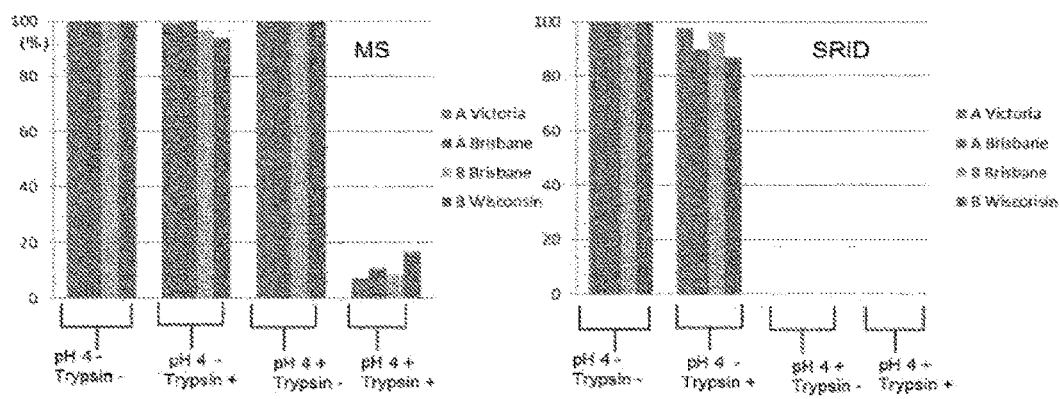

Figure 4
A
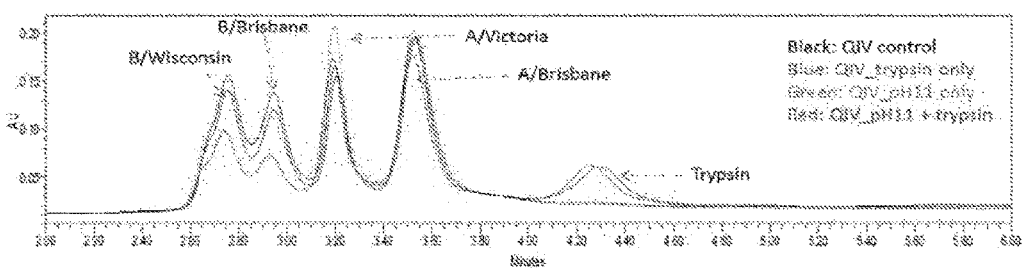
B
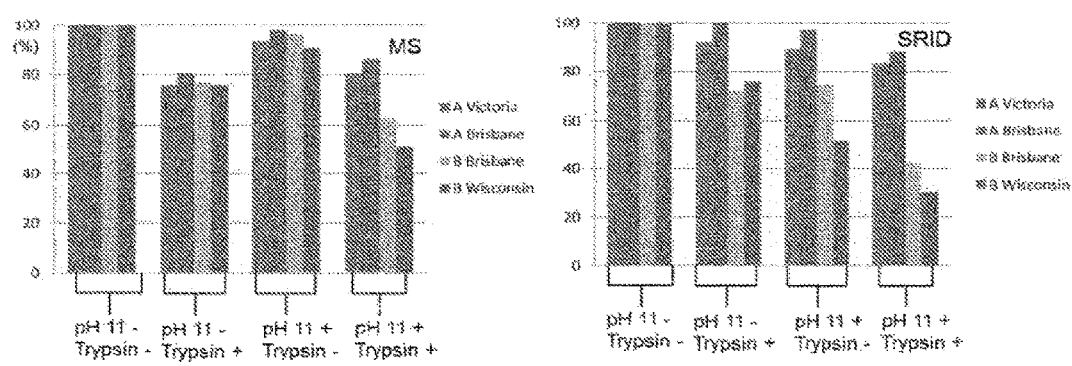

Figure 5
A
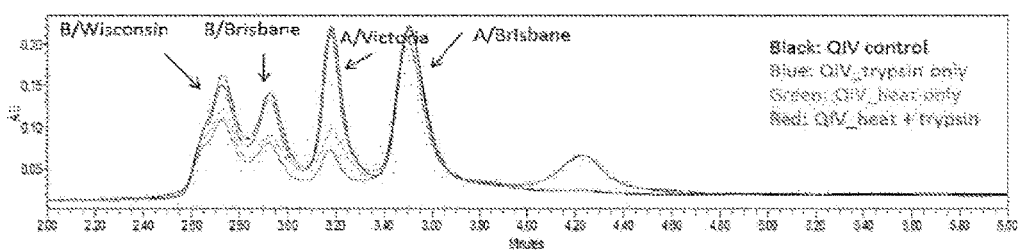
B
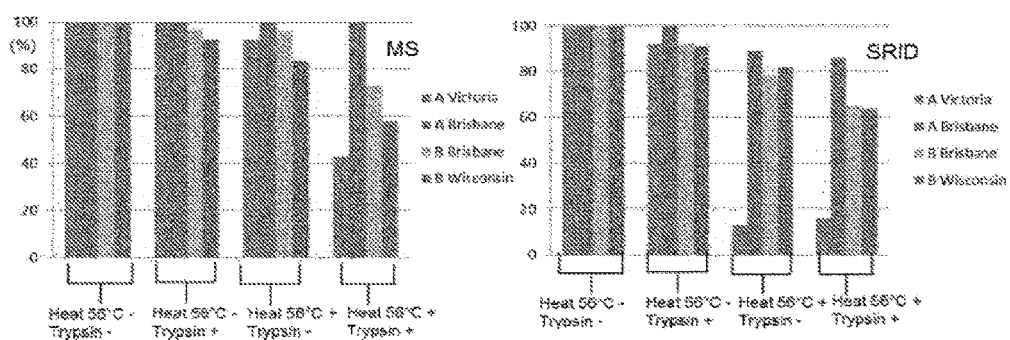

Figure 7

Peptide Behavior in Acetone wash Three times with three Strains

| Peptides | Mixture spiked | A/Brisbane | Leftover Percentage | B/Brisbane | Leftover Percentage | A/Victoria | Leftover Percentage |
|---|---|---|---|---|---|---|---|
| DEALLINGR | 497698806 | 0 | 0.00 | 2213292 | 0.44 | 3605944 | 7.25 |
| SVPEKR | 1377755649 | 4734600 | 0.34 | 6500218 | 0.47 | 10440077 | 7.61 |
| TLDFHDSNVK | 391372265 | 15505988 | 3.97 | 2097638 | 5.35 | 21307220 | 5.44 |
| GILPCR | 180009793 | 7227559 | 4.01 | 6850647 | 3.81 | 6857731 | 3.68 |
| ALSSGLR | 149767298 | 9984013 | 6.68 | 872329 | 0.58 | 5450687 | 3.65 |
| GESGVK | 209650730 | 0 | 0.00 | 453044 | 0.13 | 282057 | 0.13 |

Peptide Behavior in 2 times Acetone wash followed by 1 ethanol wash with three strains

| Peptides | Mixture spiked | A/Brisbane | Residule Percentage | B/Brisbane | Residule Percentage | A/Victoria | Residule Percentage |
|---|---|---|---|---|---|---|---|
| DEALLINGR | 479694439 | 2082950 | 0.43 | 1752469 | 0.36 | 24306160 | 5.07 |
| SVPEKR | 1321255499 | 2078496 | 1.57 | 2677870 | 2.02 | 4268293

Figure 8
A
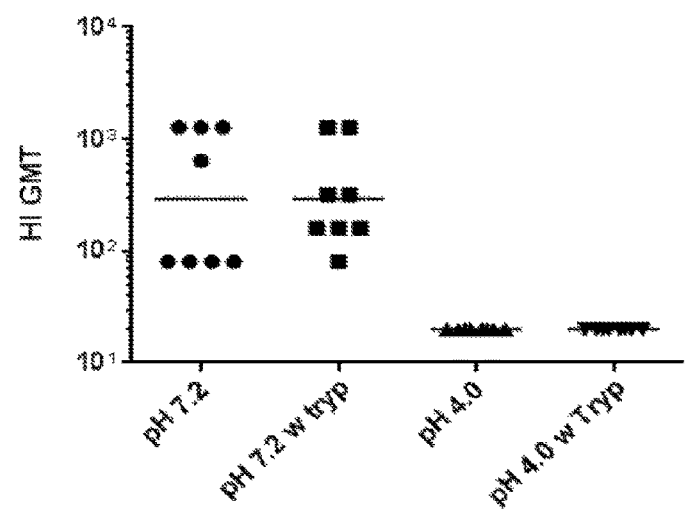
B
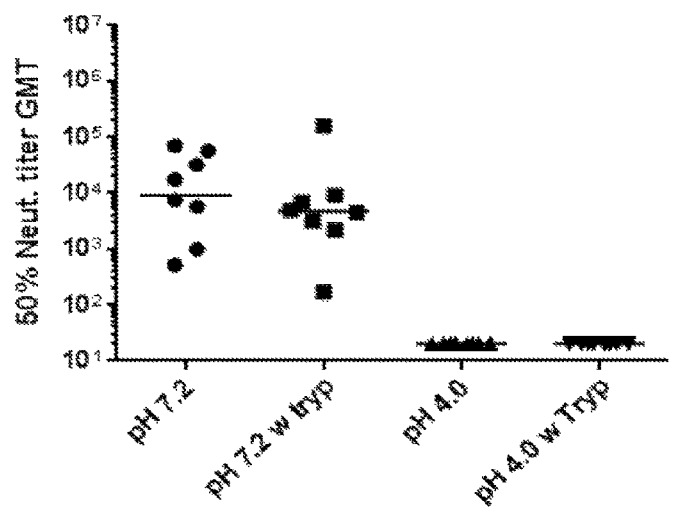

Figure 9:
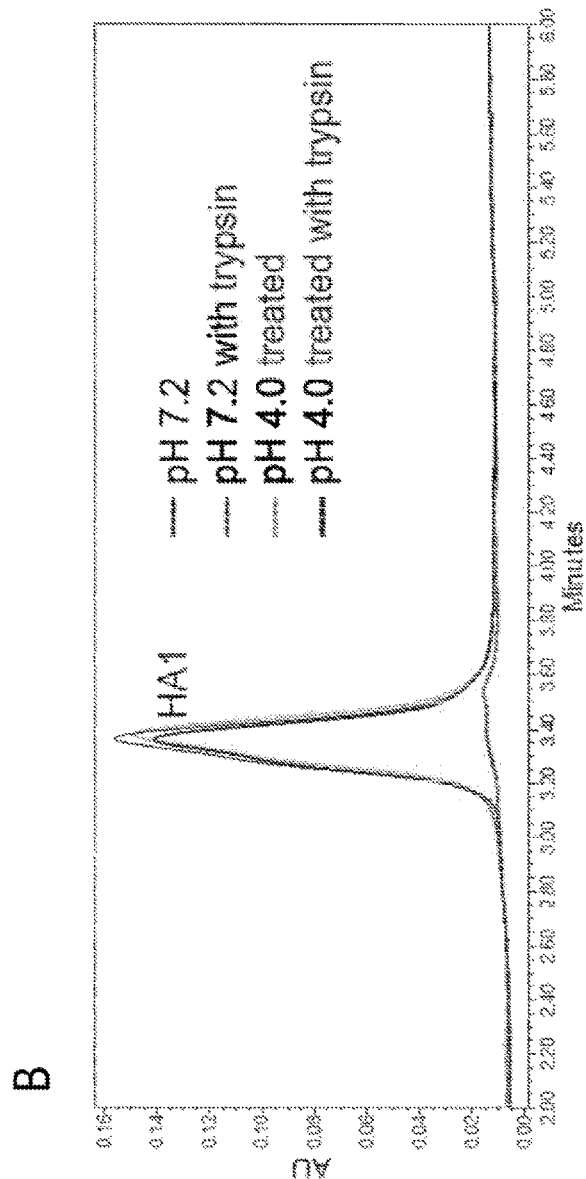

Figure 9
A
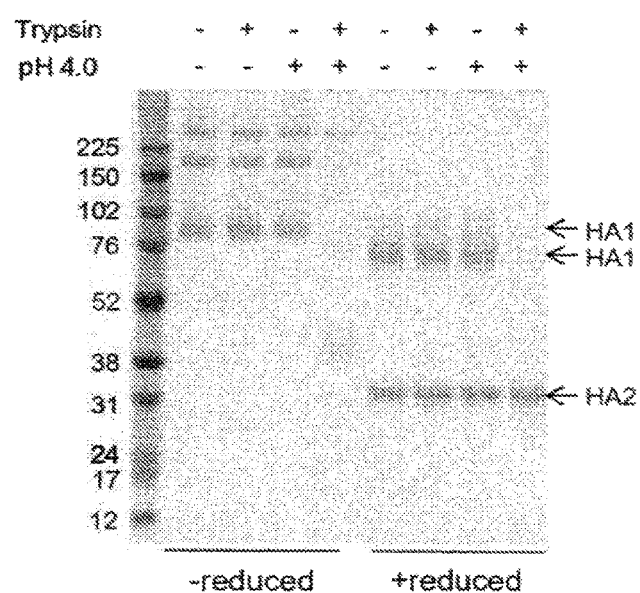
C
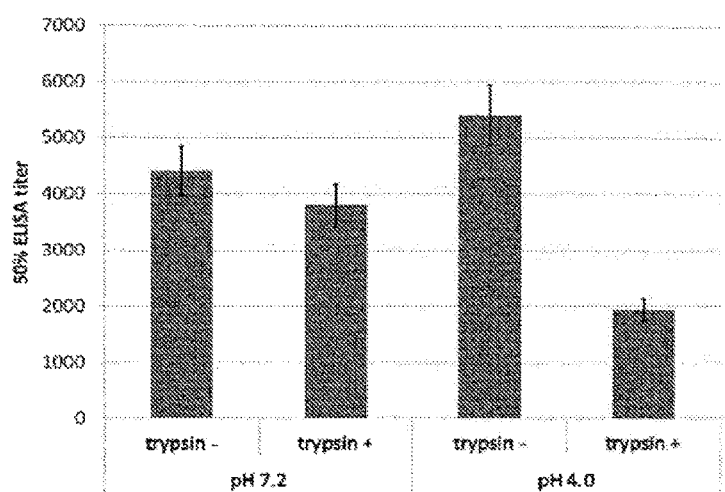

Figure 9
D
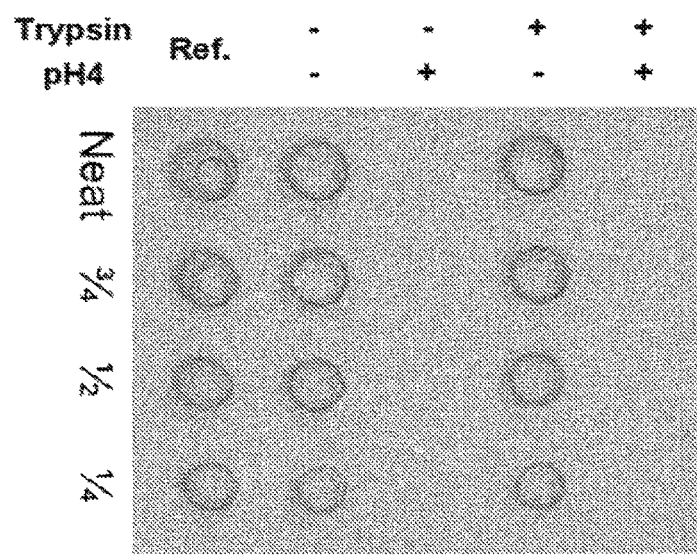
E
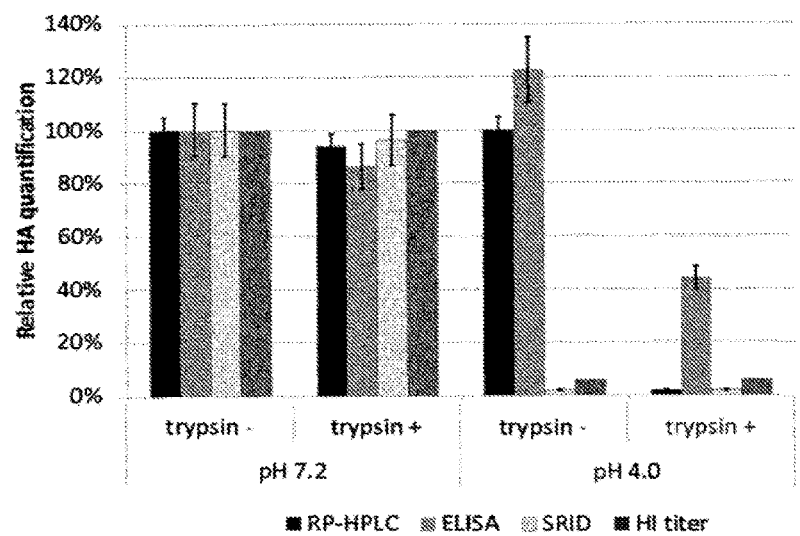

Figure 10
A
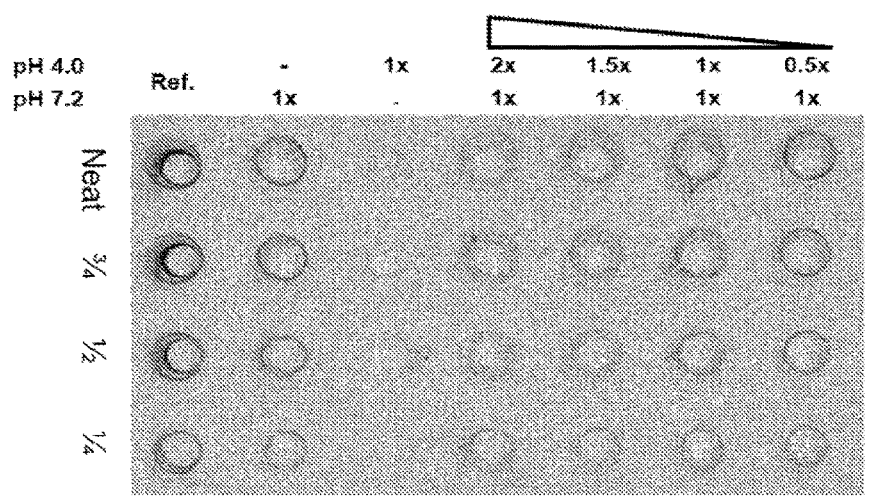
B
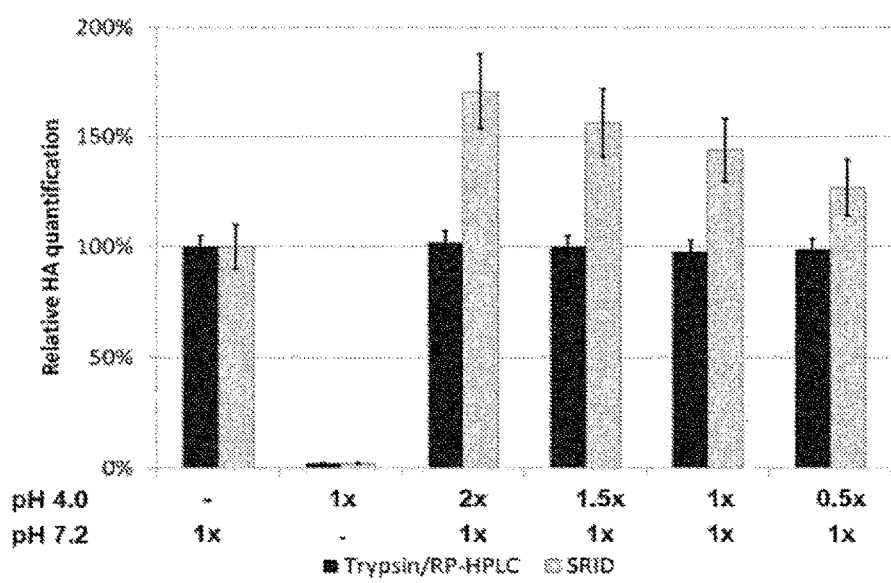

Figure 11:
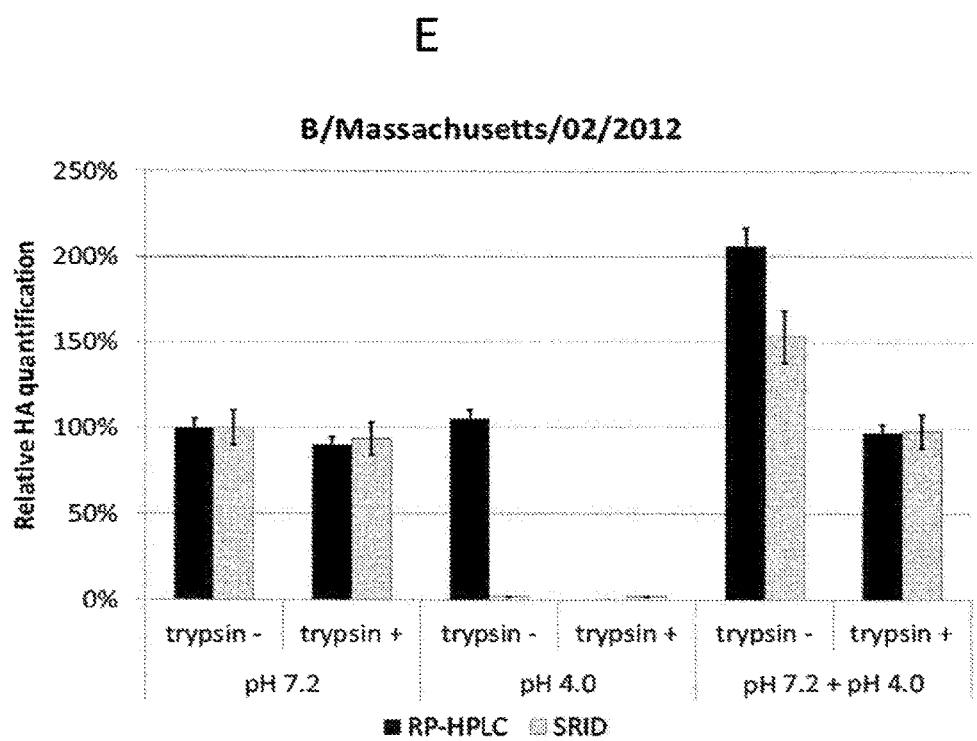
Figure 12:
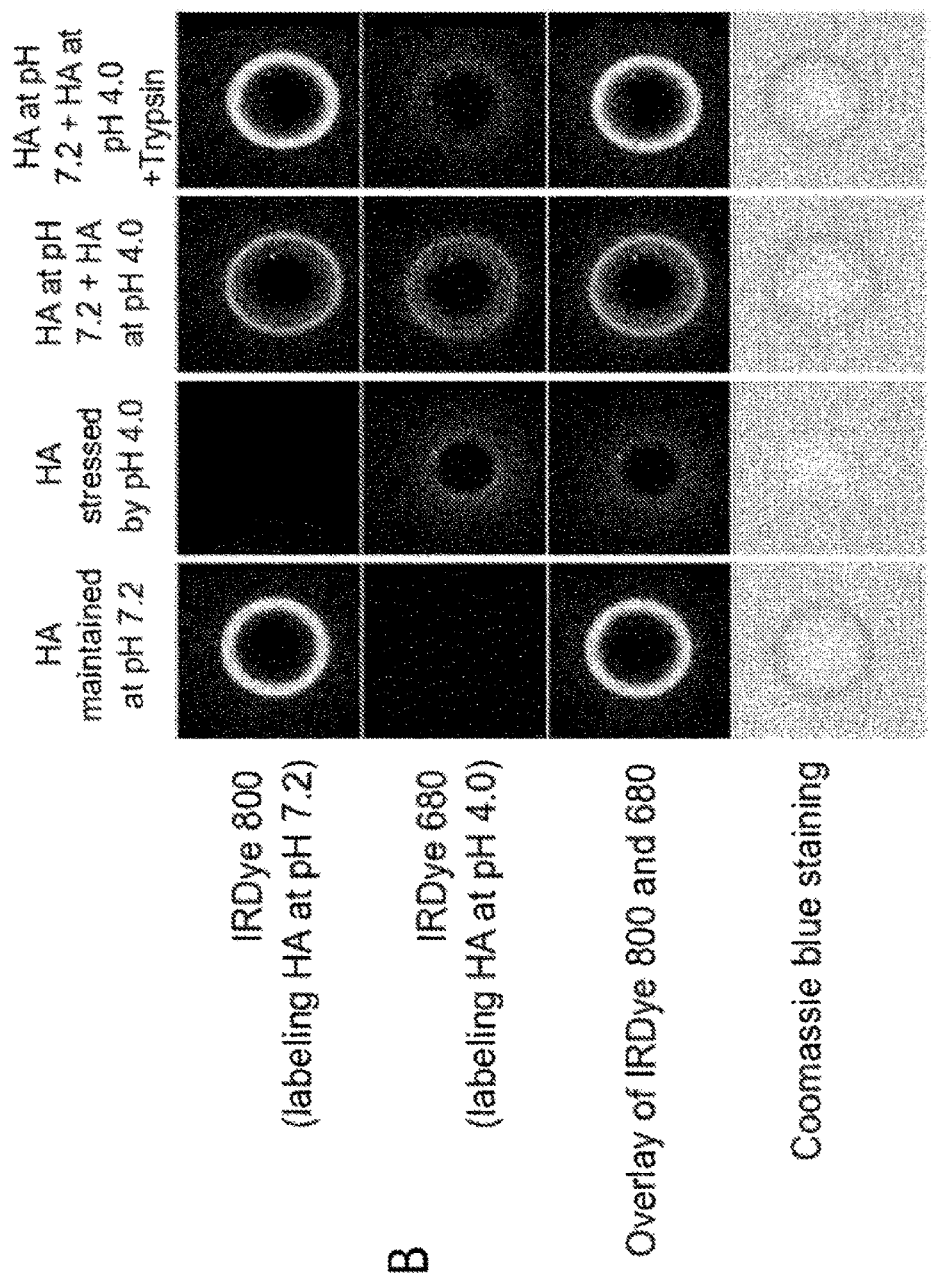

Figure 11
A
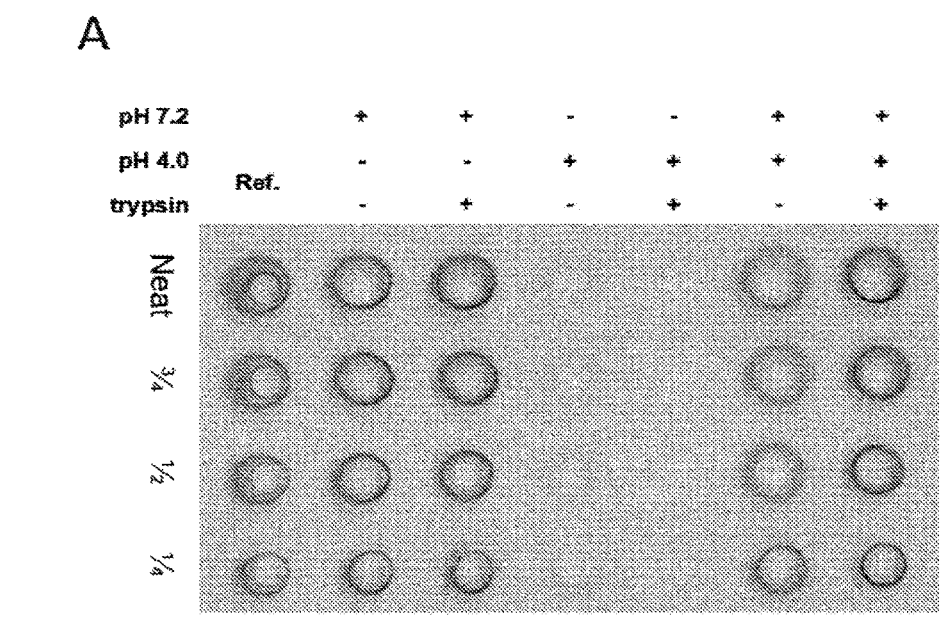
B
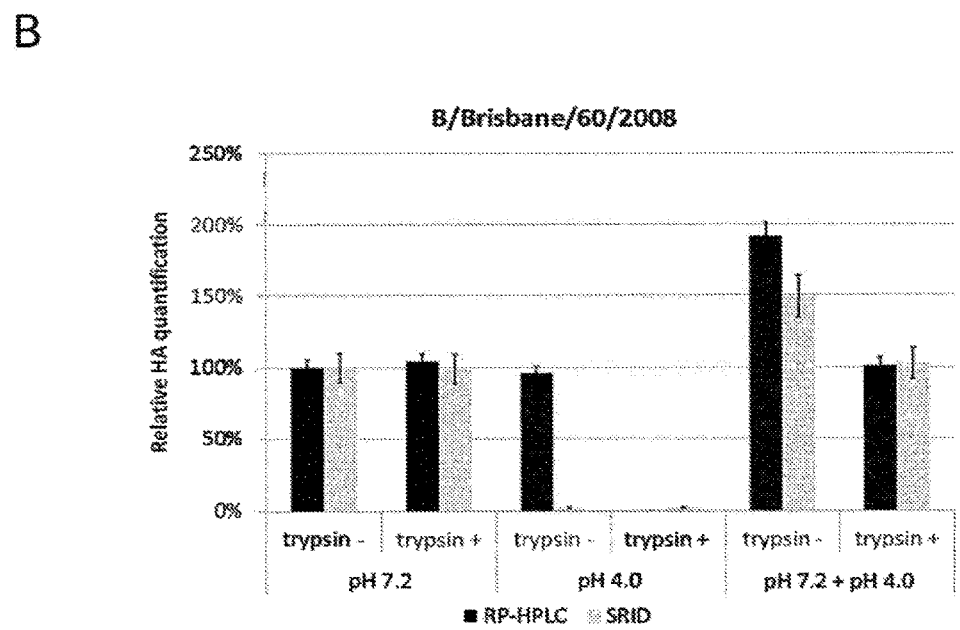

Figure 11
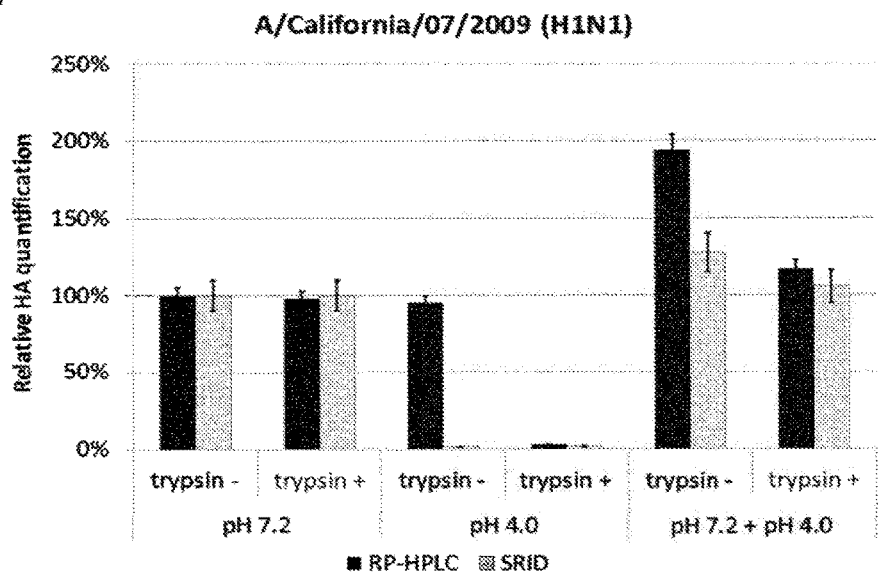
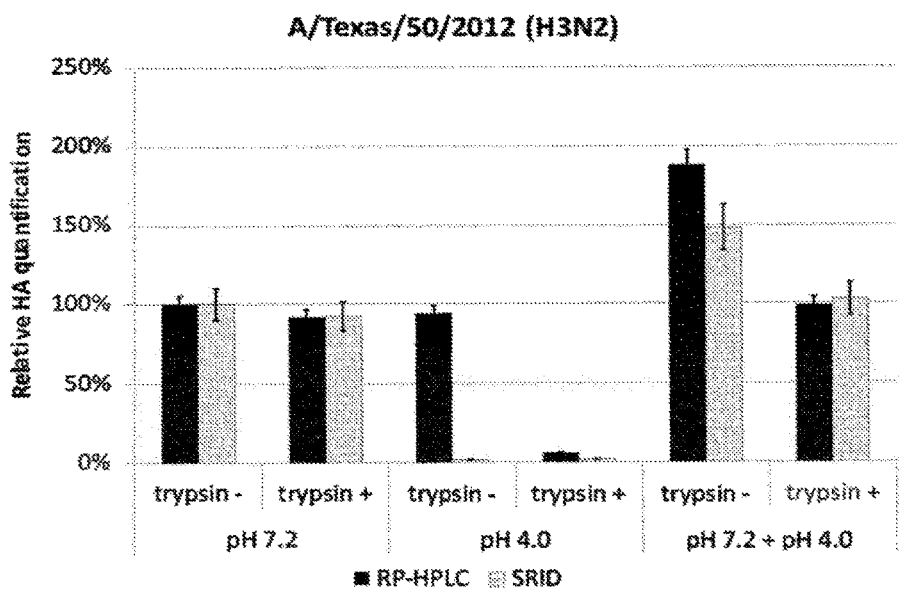

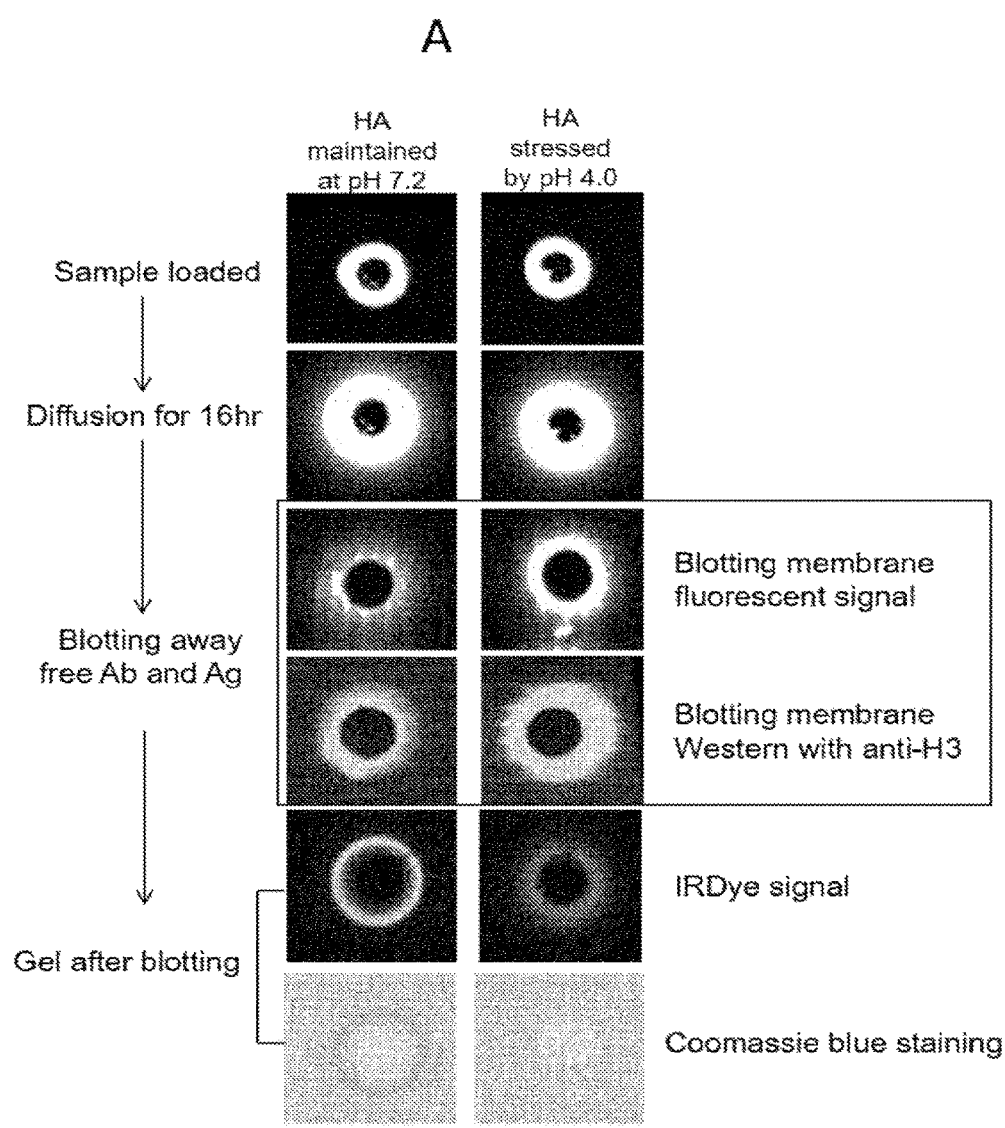

```
SEQUENCE LISTING

<160> NUMBER OF SEQ ID NOS: 6

<210> SEQ ID NO 1
<211> LENGTH: 8
<212> TYPE: PRT
<213> ORGANISM: Influenza virus

<400> SEQUENCE: 1

Asp Glu Ala Leu Leu Asn Asn Arg
1               5

<210> SEQ ID NO 2
<211> LENGTH: 7
<212> TYPE: PRT
<213> ORGANISM: Influenza virus

<400> SEQUENCE: 2

Ser His Phe Ala Asn Leu Lys
1               5

<210> SEQ ID NO 3
<211> LENGTH: 11
<212> TYPE: PRT
<213> ORGANISM: Influenza virus

<400> SEQUENCE: 3

Thr Leu Asp Phe His Asp Ser Asn Asn Val Lys
1               5                   10

<210> SEQ ID NO 4
<211> LENGTH: 7
<212> TYPE: PRT
<213> ORGANISM: Influenza virus

<400> SEQUENCE: 4

Gly Ile Leu Leu Pro Gln Lys
```

-continued

```
1               5

<210> SEQ ID NO 5
<211> LENGTH: 10
<212> TYPE: PRT
<213> ORGANISM: Influenza virus

<400> SEQUENCE: 5

Asn Leu Asn Ser Leu Ser Glu Val Glu Lys
1               5                   10

<210> SEQ ID NO 6
<211> LENGTH: 7
<212> TYPE: PRT
<213> ORGANISM: Influenza virus

<400> SEQUENCE: 6

Glu Glu Ile Ser Gly Val Lys
1               5
```

INFLUENZA POTENCY ASSAYS

This application is a national stage filing under 35 U.S.C. § 371 of International Application No. PCT/EP2016/066200, filed on Jul. 7, 2016, which claims priority of European Patent Application No. 15175765.5, filed Jul. 7, 2015, and European Patent Application No. 16152829.4, filed Jan. 26, 2016. The contents of these applications are each incorporated herein by reference.

SEQUENCE LISTING

The instant application contains a Sequence Listing which has been filed electronically in ASCII format and is hereby incorporated by reference in its entirety. Said ASCII copy was created on Mar. 25, 2019.

FIELD OF THE INVENTION

This invention relates generally to vaccines, more specifically to assays for influenza vaccines.

BACKGROUND TO THE INVENTION

Recent outbreaks of influenza highlight the need to rapidly produce and release adequate amounts of influenza vaccines to protect the general public from this disease, which has potentially deadly complications.

The standard assay for hemagglutinin (HA) content in inactivated influenza vaccines is based on single radial immunodiffusion ("SRID") (refs. 1 & 2) which was recommended by the WHO in 1978 to replace tests based on agglutination of erythrocytes.

Although the SRID assay is well established, it is slow to perform, has poor dynamic range, is susceptible to considerable variability, and it can take a long time to prepare and calibrate the required specific anti-HA serum. As the influenza strains in vaccines change every season, this creates a bottleneck for influenza vaccine lot release because these reference reagents need to be prepared and calibrated anew for every strain change. This is particularly problematic in the case of an influenza pandemic where influenza vaccines need to be prepared as quickly as possible.

Another drawback of the SRID assay is that it may not reliably distinguish between immunogenically active forms of the influenza hemagglutinin (HA) antigen and those which are not as immunogenic because the antisera used in the assay may not be completely specific and may react with both forms, although it is generally thought that such antisera can be adjusted to preferentially recognize the native, immunogenic form in the SRID assay (ref. 125). As the immunogenicity (hence the immunoprotection) of an influenza vaccine is determined by the amount of immunogenically active HA, it is desirable for an assay to be able to specifically measure the immunogenically active form of HA.

Reference 3 suggests an alternative to a SRID assay in which ultrafiltration is followed by reverse phase high pressure liquid chromatography (RP-HPLC), and references 4 and 5 teach high pressure liquid chromatography (HPLC) based assays. References 6 and 7 developed quantitative mass spectrometry based assays. These assays could accurately quantify total HA and did not depend on strain-specific antisera, but failed to differentiate immunologically active HA from inactive HA. An ELISA assay was able to specifically quantify immunologically active HA but relied on generation of strain specific antibodies (ref. 8), which significantly increases the time needed before the vaccine can be released.

SUMMARY OF THE INVENTION

The present invention encompasses identifying the source of problems with the existing influenza potency assays. Thus, the invention is based at least in part on the recognition that conventional methods used to quantify influenza virus antigens for vaccine production do not accurately measure the amount of influenza virus proteins included in vaccines as immunogens. Work presented herein and elsewhere suggests that an isolated influenza viral protein may act as an antigen in in vitro immunoassays, but not as a functional immunogen to elicit an immune response in vivo. There is dire need to differentially measure these functionally and structurally distinct forms of influenza proteins, so influenza vaccines can be manufactured to reflect accurate amounts of functional immunogens contained therein. To that end, the inventors of the present disclosure sought to develop an assay based on biophysical measurements (as opposed to immunochemical measurements) to distinguish structural differences between active, immunogenic conformations and inactive counterparts. The rationale for this approach includes: i) more direct assessment of the proteins/antigens themselves; ii) speed by which such assays can be carried out; ill) simplicity by which a sample with multiple antigens can be simultaneously processed; and/or, iv) no necessity for reliance on the availability of corresponding antisera (typically sheep antisera).

Accordingly, the methods provided herein enable vaccine manufacturers to accurately indicate how much immunogenic antigen is contained in their respective vaccines, not merely the total amount of proteins included in the products. This is important from a public health perspective, because it is necessary to determine how much immunogenic HA is present and also is desirable to know how much non-functional HA is present in vaccines, and because it helps to shift the focus more on the purity and efficacy of vaccines.

It is therefore an object of the invention to provide an influenza potency assay which is faster than the traditional SRID assay and further provides a more reliable assessment of the amount of immunogenically active HA in an influenza vaccine.

The invention further provides an improved SRID assay, in which the traditional SRID assay has been modified to take advantage of the benefit of biological proteolysis described herein, i.e., the ability to differentiate between the immunogenic form of HA and the poorly immunogenic form of HA. Thus, another aspect of the invention provides, an SRID assay which incorporates a step of biological proteolysis (e.g., trypsin pre-treatment) prior to SRID, thereby improving accuracy of the assay in determining the amount of immunologically active HA in a sample. Suitable samples may be samples as defined herein. Suitable samples may be obtained from, for example, antigen bulk preparations (such as monobulk), intermediate preparations, during manufacture and/or after final formulation, final vaccine formulations and/or products prior to release, vaccine products after storage, etc. SRID with pre-treatment by biological proteolysis, as described herein, advantageously avoids overestimation of immunologically active HA seen in traditional SRID formats.

The methods described herein are suitable for measuring the amount of influenza viral antigens during the manufacture of influenza vaccines, as well as for quality control purposes, e.g., evaluating the potency of samples (including intermediate preparations, bulk preparations, and final vaccine products) after durations of time, e.g., after storage.

BRIEF DESCRIPTION OF DRAWING

FIG. 1 shows that low pH-induced post fusion HA1 is sensitive to trypsin digestion while control pre-fusion HA1 is resistant to trypsin even at high protease concentration, as shown by both reduced SDS-PAGE (A) and RP-HPLC (B).

FIG. 2 provides a flow chart of the influenza potency assay.

FIG. 3 provides results from pH 4-stressed quadrivalent influenza vaccine (QIV) sample tested by an assay of the present invention and SRID. (A) RPLC chromatogram of the differentially treated samples (annotation of the peaks are based on retention times of the standard monobulks); (B) assay results by the current assay (left panel) and SRID (right panel). Potency of each strain at –/– control is shown as 100%.

FIG. 4 provides results from pH 11-stressed quadrivalent influenza vaccine (QIV) sample tested by an assay of the present invention and SRID. (A) RPLC chromatogram of the differentially treated samples (annotation of the peaks are based on retention times of the standard monobulks); (B) assay results by the current assay (left panel) and SRID (right panel). Potency of each strain at –/– control is shown as 100%.

FIG. 5 provides results from heat (56° C.)-stressed quadrivalent influenza vaccine (QIV) sample tested by the current assay and SRID. (A) RPLC chromatogram of the differentially treated samples (annotation of the peaks is based on retention times of the standard monobulks); (B) assay results by the current assay (left panel) and SRID (right panel). Potency of each strain at –/– control is shown as 100%.

FIG. 6 shows percentage of immunogenic HA recovered following acetone precipitation for A/Victoria, A/Brisbane and B/Brisbane strains.

FIG. 7 provides a table detailing the percentage of digested inactive HA peptides that remain following different washing protocols. Samples were washed i) three times in acetone; ii) twice in acetone followed by a single ethanol wash; or iii) three times in ethanol. Washing three times in ethanol produced the best result by removing the greatest amount of digested inactive HA peptides.

FIG. 8 provides graphs showing immunogenicity in mice of two injections of 1 μg egg-produced A/Texas/50/2012 (H3N2) HA maintained at pH 7.2 or transiently exposed to pH 4.0, with and without trypsin digestion. (A) HI titers using A/Texas/50/2012 (H3N2) virus and turkey blood cells. (B) Microneutralization titers in the same set of sera as A using A/Texas/50/2012 (H3N2) virus to infect MDCK cells.

FIG. 9 shows SDS-PAGE, RP-HPLC, ELISA and SRID analysis of egg-produced A/Texas/50/2012 (H3N2) HA maintained at pH 7.2 or transiently exposed to pH 4.0, with and without trypsin digestion. (A) SDS-PAGE of non-reduced (left) and reduced (right) samples. (B) Analytical RP-HPLC chromatograms of the same set of samples as in (A). (C) ELISA of the same set of samples as in (A), performed with HA coated on plates and detected by the sheep polyclonal antiserum used in SRID. (D) SRID gel image for the same set of samples as in (A). (E) Summary of HA quantification by RP-HPLC, ELISA and SRID with HI titer from immunogenicity in mice.

FIG. 10 shows SRID and trypsin/RP-HPLC analyses for homogeneous samples of egg-produced A/Perth/16/2009 (H3N2) HA maintained at pH 7.2 or transiently exposed to pH 4.0 and for mixtures of the two samples. (A) Image of an SRID gel assaying non-stressed HA, low-pH stressed HA and non-stressed HA spiked with 2×, 1.5×, 1× and 0.5× of low-pH stressed HA. (B) Relative quantification of HA from the SRID gel in A and from trypsin/RP-HPLC assay of the stressed samples and their mixtures.

FIG. 11 shows SRID and RP-HPLC analysis for HA maintained at pH 7.2 or transiently exposed to pH 4.0 or the mixture of the two HA samples with and without trypsin digestion. (A) SRID image for egg-produced B/Brisbane/60/2008 samples subject to these treatments. (B) HA quantification by SRID and RP-HPLC for egg-produced B/Brisbane/60/2008 HA; (C) A/California/07/2009 (H1N1) HA; (D) A/Texas/50/2012 (H3N2) HA; and (E) B/Massachusetts/02/2012 HA; subject to these treatments.

FIG. 12 provides images of SRID analysis of IRDye-labeled A/Texas/50/2012 (H3N2) HA. (A) Non-stressed HA and low-pH stressed HA, each labeled with IRDye800, were analyzed by SRID. The labeled protein was tracked in the SRID gel by infrared fluorescent imaging. Non-labeled HA was also detected by western blotting with an anti-H3 antibody on a nitrocellulose membrane used to blot the SRID gel. (B) Non-stressed HA was labeled with IRDye800, and low-pH stressed HA was labeled with IRDye680. The non-stressed HA, stressed HA, and a mixture of non-stressed and stressed HA with and without trypsin treatment were detected in SRID gel through the green and red channels of the imager.

DETAILED DESCRIPTION OF PREFERRED EMBODIMENTS

The invention provides methods for quantifying immunogenic HA in a sample, which are faster, more accurate and do not require the use of antisera. According to the invention, immunogenic HA and inactive HA can be separated due to their different conformation, which is reflected in their differential sensitivity to proteolysis. These methods are independent from antisera and exploit a biophysical pretreatment to selectively remove immunologically inactive HA (e.g., poorly immunogenic, stressed or post-fusion conformations), followed by separation and quantification of the immunogenic HA. These methods are therefore significantly faster than the standard SRID assay and are further more accurate because only the amount of immunogenic HA is measured.

The invention provides a method comprising the steps of:

a) providing a sample comprising immunogenic HA, inactive HA, or combination thereof;

b) subjecting the sample to biological proteolysis, wherein the inactive HA is digested and the immunogenic HA remains undigested;

c) separating the digested inactive HA from the undigested immunogenic HA in the sample;

d) subjecting the undigested immunogenic HA to analytical proteolysis, so as to provide fragments of digested immunogenic HA; and, e) carrying out liquid chromatography-electrospray ionization-tandem mass spectrometry (LC-ESI-MS) in the presence of at least one labeled reference HA peptide, to quantify the amount of immunogenic HA in the sample.

Further provided is a method for quantifying immunogenic influenza HA in a sample, comprising the steps of:

a) subjecting the sample to biological proteolysis;
b) separating the immunogenic HA from other components in the sample; and,
c) quantifying the immunogenic HA in the sample.

In a particularly preferred embodiment, step (c) is carried out using mass spectrometry, in particular liquid chromatography-electrospray ionization-tandem mass spectrometry (LC-ESI-MS).

The quantification of the immunogenic HA can in principle be performed using any method for protein quantification known in the art. Certain embodiments described above would also be compatible with quantification by SRID.

Also provided are methods as described herein wherein a step of separating the immunogenic HA from other components in the sample (e.g. separating the digested inactive HA from the undigested immunogenic HA in the sample) is dispensed with. Such methods may be an alternative to the methods described herein that involve a separation step, particularly the methods wherein quantification is by mass spectrometry. Such methods have the advantage of reducing the number of processing or handling steps (e.g. by eliminating a step of separation by protein precipitation) and minimizing sample loss. The inventors have found that one can further differentiate the quantity of immunogenic HA from inactive HA in a sample if different proteases, or different selections of proteases, having different substrate specificities (or selections of substrate specificities), are used in each of the biological and analytical proteolysis steps. In such methods, the inactive HA is digested by one or more proteases in the biological proteolysis step, to produce digested inactive HA, while the immunogenic HA (or substantially all of the immunogenic HA), remains undigested. The mixture of undigested immunogenic HA and digested inactive HA is then subjected to analytical proteolysis by one or more proteases. Importantly, the analytical proteolysis is carried out using a protease or selection of proteases that cannot cleave the immunogenic HA at one or more cleavage site(s) which can be cleaved in the inactive HA during biological proteolysis. In this way, the analytical proteolysis can provide fragments of digested immunogenic HA that comprise immunogenic HA-derived peptide(s) that is/are distinguishable from the inactive HA-derived peptides. For example, the fragments of digested immunogenic HA will comprise one or more immunogenic HA-derived peptide(s) which contain at least one cleavage site that can be cleaved by at least one protease, wherein the at least one protease was used in the biological proteolysis step, but not in the analytical proteolysis step.

Accordingly, the invention also provides a method comprising the steps of:
a) providing a sample comprising immunogenic HA, inactive HA, or combination thereof;
b) subjecting the sample to biological proteolysis by one or more proteases, wherein the inactive HA is digested and the immunogenic HA remains undigested;
c) subjecting the mixture of undigested immunogenic HA and digested inactive HA to analytical proteolysis using one or more proteases, wherein the analytical proteolysis cannot cleave the immunogenic HA at one or more cleavage site(s) which can be cleaved in the inactive HA during biological proteolysis, so as to provide fragments of digested immunogenic HA that comprise immunogenic HA-derived peptide(s) that is/are distinguishable from the inactive HA-derived peptides; and,
d) carrying out liquid chromatography-electrospray ionization-tandem mass spectrometry (LC-ESI-MS) in the presence of at least one labeled reference HA peptide, to quantify the amount of immunogenic HA in the sample.

In preferred embodiments of these methods, one protease (e.g. a chymotrypsin-like protease) is used the biological proteolysis step and a different protease having a different substrate specificity (e.g. a trypsin-like protease) is used in the analytical proteolysis step. Alternatively, more than one different protease (e.g. two) may be used in the biological proteolysis step and a single protease may be used in the analytical proteolysis step. If a set of more than two different proteases (e.g. three, four or more) is used in the biological proteolysis step, a set of fewer different proteases may be used in the analytical proteolysis step.

Such methods may, for example, involve subjecting the sample to biological proteolysis by a first protease and a second protease, wherein the substrate specificity of the second protease is different to that of the first protease. The methods may then involve subjecting the mixture of undigested immunogenic HA and digested inactive HA to analytical proteolysis by only the first protease. Alternatively, a third protease having a substrate specificity that is different to that of both the first and second proteases may be used in the analytical proteolysis. In some embodiments, first and second proteases are used for the biological proteolysis, wherein the first protease is a trypsin-like protease (e.g. trypsin) and the second protease is a chymotrypsin-like protease (e.g. chymotrypsin).

The analytical proteolysis may use a single protease. In particularly preferred embodiments, the single protease used for analytical proteolysis is a trypsin-like protease (e.g. trypsin).

Further examples of suitable proteases are provided below and would be known to a person skilled in the art. Suitable combinations of proteases for use in the invention can be easily determined by a skilled person in a pilot experiment. It will also be appreciated by a person skilled in the art that a reference/surrogate HA peptide(s) used for immunogenic HA quantification may be selected to comprise an HA sequence which contains at least one cleavage site that can be cleaved by at least one protease, wherein said at least one protease is used in the biological proteolysis step, but not in the analytical proteolysis step. For example, a surrogate HA peptide used for immunogenic HA quantification may be selected which comprises an HA sequence which is cleaved by a chymotrypsin-like protease (e.g. chymotrypsin) when the chymotrypsin-like protease is used in the biological proteolysis step (e.g. either alone or along with a trypsin-like protease such as trypsin), but not in the analytical proteolysis step.

In another aspect, the invention provides improved SRID methods for quantifying immunogenic HA in a sample, which are more accurate than standard SRID assays. As explained above, immunogenic HA and inactive HA can be separated due to their different conformation, which is reflected in their differential sensitivity to proteolysis. The SRID methods of the invention typically use an antiserum (i.e., they are not independent from antisera) and also exploit a biophysical pretreatment to enable selective removal of immunologically inactive HA (e.g., poorly immunogenic, stressed or post-fusion conformations). In the SRID methods of the invention, this pretreatment (biological proteolysis) is followed by quantification of the immunogenic HA.

Thus, the invention further provides a method for quantifying immunogenic influenza HA in a sample, comprising the steps of:

a) subjecting the sample to biological proteolysis; and,
b) quantifying the amount of immunogenic HA in the sample from (b) by a SRID assay.

In some embodiments, the SRID assay of step (b) is carried out with the use of an antiserum, such as polyclonal antisera (e.g., sheep polyclonal antisera) and/or a monoclonal antibody antiserum (e.g., comprising suitable monoclonal antibodies). Suitable antiserum or antisera is/are strain-specific and may be HA-specific. Thus, the SRID assay may be carried out with the use of strain-specific, anti-HA, polyclonal (sheep) antisera.

The invention further provides a method for manufacturing an influenza vaccine, the method comprising steps of:
a) providing a sample from a bulk preparation comprising an influenza HA;
b) quantifying the amount of immunogenic HA according to a method of the invention; and,
c) packaging unit dosage forms from the bulk preparation according to the amount of immunogenic HA in the sample.

The invention further provides a method for preparing an influenza vaccine, comprising the steps of:
a) quantifying the amount of HA in a bulk vaccine by a method of the invention; and
b) preparing a vaccine from the bulk.

Biological Proteolysis and Analytical Proteolysis

Influenza viral surface HA primarily exists as an oligomer (such as a trimer) in the pre-fusion state, which is the most immunologically relevant state. Under various stress conditions, HA can undergo an irreversible transition to post-fusion state, which does not elicit a good immune response. The preparation of influenza vaccines often results in the presence of post-fusion HA and the standard SRID assay cannot distinguish between pre-fusion (immunogenic) and post-fusion (inactive) HA, thus resulting in an overestimation of the actual amount of immunogenic HA contained in the vaccine. The methods of the invention distinguish between these different forms of HA by biological proteolysis so that only the immunogenic form is quantified.

Accordingly, as used herein, "biological proteolysis" refers to an enzyme-based digestion of HA, whereby immunologically active forms of the protein (e.g., HA in the pre-fusion state) remain intact (i.e. undigested), while inactive forms of the protein (e.g., HA in the post-fusion state) become digested. A step of biological proteolysis therefore achieves differential digestion, depending on the conformation of the protein. HA proteins that have not undergone a denaturation step are resistant to biological proteolysis. Thus, a step of biological proteolysis, as used herein, achieves controlled or limited digestion of the protein, depending on the structural integrity or conformation of the protein.

By contrast, as used herein, "analytical proteolysis" refers to fragmentation (i.e., digestion) of a target protein regardless of its conformation, typically for purposes of subsequent analytical step(s), such as mass spec analyses. Analytical proteolysis involves a step of denaturing the protein before digestion.

It was reported in reference 9 that the conformation of HA changed depending on the pH and that some forms of HA were susceptible to protease digestion whilst others were not. This could be attributed to the well-packed structure and dense glycosylation coat on the surface of immunogenic HA. The inventors have confirmed that pre-fusion HA is very resistant to proteolytic degradation in its native state even at a high protease concentration (HA:Trypsin=5:1). In contrast, low pH induced post fusion HA1, even when native, was very sensitive to proteolytic degradation.

By including a step of biological proteolysis before quantification, the methods of the invention allow a distinction between immunogenic HA and inactive HA. In particular, immunogenic HA is protease-resistant whilst the inactive HA is protease-sensitive. This means that substantially all of the inactive HA becomes digested whereas substantially all of the immunogenic HA remains structurally intact when a protease is added to the sample (for example, where trypsin is added at an enzyme:substrate ratio of 1:20 and incubated at 37° C. for 2 hours). The biological proteolysis step therefore digests substantially all of the inactive (post-fusion) HA whilst substantially all of the immunogenic (pre-fusion) HA remains undigested. In this respect, it will be understood that the immunogenic HA is not entirely resistant to protease-dependent cleavage per se. In particular, HA0 can be cleaved by certain proteases (such as trypsin) into HA1 and HA2 but the protein does not become dissociated into fragments. Rather, HA1 and HA2 remain associated as a complex which maintains the same structural integrity (e.g., pre-fusion state). These HA1/HA2 complexes are still considered to be immunogenic. The cleaved pre-fusion HA can be distinguished from the digested products of inactive HA in that substantially all of the inactive HA is fragmented into peptides by the protease.

"Substantially" in the context of proteolysis (digestion) means that at least 80%, 85%, 90%, 95%, 96%, 97%, 98%, or 99% of the inactive (post-fusion) HA present in a sample is digested. Likewise, "substantially" in the context of immunogenic HA means that at least 80%, 85%, 90%, 95%, 96%, 97%, 98%, or 99% of the immunogenic (pre-fusion) HA remains undigested.

The immunogenic HA is in the form of a pre-fusion HA trimer, a pre-fusion HA oligomer (e.g., so called rosettes) or combinations thereof. The inactive HA is an HA monomer, a post-fusion HA trimer, a denatured protein, an aggregated protein, or a combination thereof. The pre-fusion and post fusion HA configurations can be identified, for example, using methods known in the art such as crystallography.

The immunogenic HA will generally elicit a much higher immune response compared to the inactive HA. For example, the geometric mean titre (GMT) obtained from injecting a subject with the immunogenic HA may be at least 2 times, at least 4 times, at least 8 times or at least 16 times higher with the immunogenic HA compared to the inactive HA. Thus, it should be readily understood by those skilled in the art that the "inactive HA" as used herein (e.g., post-fusion, or stressed forms of HA) does not necessarily mean it completely lacks immunogenicity; rather, it is poorly immunogenic as compared to pre-fusion, non-stressed forms of HA that are trypsin-resistant.

The biological proteolysis can be performed with any protease that can digest inactive HA. Such enzymes are known in the art and include, for example, serine proteases (such as trypsin), threonine proteases, cysteine proteases, aspartate proteases, glutamic acid proteases, and metalloproteases. Exemplary serine proteases include, without limitation, trypsin-like proteases, chymotrypsin-like proteases, elastase-like proteases and subtilisin-like proteases. All of these enzymes are expected to work in the methods of the invention as the different proteolytic activity in respect of immunogenic HA and inactive HA is due to the well packed structure and dense glycosylation coat on the surface of immunogenic HA which physically prevents proteases from digesting the protein. Indeed, the inventors have also shown that chymotrypsin can digest inactive (post-fusion) HA in a biological proteolysis step. Thus, biological proteolysis may use trypsin and/or chymotrypsin. The methods of the invention may be practiced using two, three, four or more proteases.

Methods for determining whether a protease can digest inactive HA are well known in the art. For example, a skilled person can provide inactive HA using the method described in reference 9 and test different proteases to establish which one can digest the inactive HA.

A group of proteases known to digest inactive HA are serine proteases. These are enzymes that cleave peptide bonds in proteins, in which serine serves as the nucleophilic amino acid at the active site. Such proteases are required for influenza viral infection of host cells in vivo and function by splitting the precursor HA0 into the HA1 and HA2 forms, thus allowing the influenza virus to infect the host cells by promoting membrane fusion. As serine proteases are known to digest influenza HA they are preferred for use in the invention.

The most commonly used serine protease for digesting influenza HA is trypsin and the use of this protease in the methods of the invention is particularly preferred. However, other serine proteases which can digest HA can also be used. Examples of such proteases include TMPRSS2 and HAT (ref. 10).

The protease is preferably added directly to the sample. This is preferred because it makes the quantification process easier and further avoids any overestimation of the amount of immunogenic HA due to manipulation of the sample. In some circumstances it may be desirable, however, to optimize the conditions for biological proteolysis in the sample before the protease is added. This may be necessary, for example, where the buffer in the sample does not allow for optimal protease activity. In these embodiments, the buffer in the sample may be exchanged through standard methods in the art such as, for example, dialysis. It is also possible to dilute the sample with additional buffer. It will be understood that care must be taken not to create conditions where additional inactive HA is formed, for example by lowering the buffer's pH as this could result in inaccurate quantification. Where this is unavoidable, it is still possible to quantify HA using the methods of the invention by performing a pilot experiment to determine the relative loss in immunogenic HA and correcting the result obtained from quantification by this amount.

Where influenza viruses are grown in cell culture, proteases such as trypsin are routinely added during the growth of the influenza viruses. The production process for influenza vaccines includes purification steps and so only negligible amounts of residual protease will be present in an influenza vaccine prepared from the influenza viruses. For the avoidance of doubt, the step of biological proteolysis cannot rely on residual protease which may be present but a protease needs to be added to the sample.

Suitable conditions for digestion can easily be determined by a skilled person. For example, the methods of the invention may be performed using about 2, 5, 10, 15, 20, 25, 30, 35, 40, 45, or 50 U/mL of a protease, such as trypsin. The methods of the invention may be performed using about 2, 5, 10, 15, 20, 25, 30, 35, 40, 45, 50, 60, 70, 80, 90, or 100 U/mL of a protease, such as trypsin. Many proteases need an optimal temperature of between 32° C. and 40° C., between 34° C. and 38° C. or about 37° C. and so digestion may be performed at that temperature. The exact time for digestion may vary but the reaction will generally be allowed to proceed until substantially all of the inactive HA has been digested. For example, the sample may be incubated with the protease for 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes or 170 minutes. The time needed for digestion can be easily determined by a skilled person in a pilot experiment.

A step of biological proteolysis as discussed above can also be beneficial in the vaccine manufacturing process. In particular, it is possible to include such a step in the vaccine manufacturing process which has the advantage that the resulting vaccine will predominantly contain immunogenic HA as the inactive HA would be selectively removed. Such methods will involve purification steps to remove the protease prior to formulation of the vaccine.

Accordingly, the invention encompasses a method for manufacturing a vaccine intermediate, the method comprising a step of preparing a bulk preparation comprising an antigen (such as HA mono-bulk), subjecting the bulk preparation or portion thereof to biological proteolysis so as to digest stressed or inactive forms of the antigen. The resulting intermediate can be subsequently used to formulate a vaccine product, which is enriched with protease-resistant, immunologically active form of the antigen. Thus, the invention includes a method for manufacturing a vaccine product, comprising steps of: preparing a bulk preparation comprising an antigen (such as HA mono-bulk), subjecting the bulk preparation or portion thereof to biological proteolysis; and, formulating a vaccine using the bulk preparation or portion thereof, which has been subjected to biological proteolysis. The antigen may be influenza antigen. However, the invention can be useful for any antigens, which can exist in multiple conformations such that protease-sensitivity (or protease-resistance) correlates with biological activities of interest (e.g., immunogenicity). In some embodiments, the vaccine product contains at least 60% of the antigen in immunologically active conformation, e.g., at least 60%, at least 70%, at least 80%, and at least 90%. In some embodiments, such vaccine products enriched with immunologically active antigen(s) may contain less-than-standard amounts of the antigen(s) but are able to elicit equivalent or greater immune responses in subjects, as compared to standard products that are not enriched with immunologically active forms of the antigen(s). For example, as compared to standard influenza vaccines with 15 μg HA per strain per dose, the vaccine products of the present invention may have equivalent or better efficacy or effectiveness with lower total antigens, e.g., less than 12 μg, less than 9 μg, less than 7.5 μg, less than 5 μg, less than 3.75 μg, HA per strain per dose.

The step of protease digestion may also provide an additional benefit of reversing some aggregation that may be present in an antigen preparation, thereby reducing the loss and increasing the yield of antigen per preparation.

As discussed above, in some embodiments, more than one protease may be used in the methods of the invention. Different proteases, or different sets of proteases, may be used in each of the biological and analytical proteolysis steps described herein. Each different protease may have different substrate specificity. For example, trypsin-like proteases, chymotrypsin-like proteases, elastase-like proteases and subtilisin-like proteases typically have different substrate specificities from each other. Proteases may be considered to have different substrate specificities if one is capable of cleaving a given peptide at a given cleavage site, while the other is not, under identical conditions. For example, trypsin-like proteases typically cleave peptides at the carboxyl side of the amino acids lysine or arginine (except when either is followed by proline). Chymotrypsin-like proteases typically cleave peptides at the carboxyl side of a large hydrophobic amino acid (e.g. tyrosine, tryptophan, phenylalanine, leucine). Elastase-like proteases typically cleave peptides at the carboxyl side of small, hydrophobic amino acids (e.g. glycine, alanine, and valine).

In certain embodiments, where quantification is by mass spectrometry, more than one different protease may be used in the analytical proteolysis step. As described herein, analytical proteolysis may be preceded by a separation step. In alternative embodiments described herein, the separation step may be dispensed with. In either case, the analytical proteolysis may use more than one different protease, having different substrate specificities (i.e. different cleavage sites). The use of more than one different protease in the analytical proteolysis stage may produce fragments of digested immunogenic HA that comprise immunogenic HA-derived peptide(s) that are shorter than the immunogenic HA-derived peptide(s) that would be produced when using fewer different proteases. Advantageously, shorter reference/surrogate peptides may therefore be used for quantification, thus providing greater freedom to choose reference peptide(s) having a sequence that is/are conserved in the immunogenic HA to be quantified. This technique may also be used to increase the availability of reference peptide(s) that do not contain amino acids that are prone to modification (e.g. chemical or post-translational modifications that could undesirably influence quantification results). In some preferred embodiments, where the analytical proteolysis is preceded by a separation step, the biological proteolysis uses one protease (e.g. a trypsin-like protease, such as trypsin) and the analytical proteolysis uses the same type of protease used in biological proteolysis and one or more different protease(s) having a different substrate specificity (e.g. a chymotrypsin-like protease, such as chymotrypsin).

Separation

Following digestion it is preferable that the undigested immunogenic HA is separated from other components in the sample. In particular, it is highly desirable that the undigested immunogenic HA is separated from the digested inactive HA. This is advantageous because it makes the downstream quantification easier. In particular, separating the immunogenic HA from the digested inactive HA allows quantification of immunogenic HA by methods such as mass spectrometry.

Nevertheless, as discussed above, in some embodiments of the invention, the separation step may be dispensed with, e.g. where analytical proteolysis provides fragments of digested immunogenic HA that comprise immunogenic HA-derived peptide(s) that is/are distinguishable from the inactive HA-derived peptides.

Methods for separating the immunogenic HA from other components in the sample are well known in the art and include, for example, reverse phase chromatography, size exclusion chromatography and ion exchange chromatography.

Whilst these prior art separation methods are suitable for use in some embodiments of the invention (in particular those which do not rely on mass spectrometry to quantify the immunogenic HA), the inventors have found that initial attempts using reverse phase and size exclusion chromatography were unsatisfactory due to a number of reasons: 1) neither chromatography was able to achieve optimal baseline resolution; 2) substantial sample loss on columns was observed; 3) significant variation introduced during fraction collection; 4) intense labor and lowered assay throughput associated with fraction collection, buffer exchange, and volume reduction.

It is therefore preferred that the immunogenic HA in the sample is separated from other components in the sample (in particular the digested inactive HA) by protein precipitation. The advantage of this approach includes same-tube sample preparation/processing, which minimizes sample loss; a reduced introduction of artefacts; and the convenience of resuspending recovered protein pellets in a desired volume of compatible buffer for downstream sample preparation. The inventors found that protein precipitation consistently recovered nearly 100% of the immunogenic HA in the sample.

Various methods for precipitating proteins are known in the art. They include salting out, isoelectric point precipitation, precipitation with organic solvents, non-ionic hydrophilic polymers, and flocculation by polyelectrolytes. Thus, in some embodiments, the step of separating comprises removing digested inactive HA fragments from the sample that retains intact, undigested immunogenic HA.

The inventors have seen good results with organic solvents, in particular with acetone which resulted in nearly 100% recovery of immunogenic HA from the sample. In a preferred embodiment the step of separating the (undigested) immunogenic HA comprises a step of adding an organic solvent, in particular a ketone or alcohol. The organic solvent may be acetone, ethanol or methanol. The methods of the invention may further include a step of washing the precipitated protein with an alcohol. The added alcohol may have a temperature of less than 4° C. The alcohol is preferably ethanol. The inventors found that this step effects complete removal of the digested peptides derived from the inactive HA. The precipitant may then be dried, for example by air drying or vacuum centrifugation.

Following protein precipitation, the precipitated protein is resuspended. This can be achieved, for example, by adding a buffer that introduces strong denaturing conditions, such as a strong denaturing guanidine buffer. The sample may further be heated to facilitate protein resuspension. Such methods are standard in the art and a skilled person can therefore easily put them into practice.

As shown in the Examples below, where the step of quantifying immunogenic influenza HA uses a SRID assay, the SRID assay itself may enable separation of immunogenic HA from other components in the sample (e.g. inactive HA).

Quantification

The quantification of the immunogenic HA can in principle be performed using any method for protein quantification known in the art. For example, the methods of the invention would be compatible with quantification by SRID as the step of digesting the inactive HA, as described above, allows for a more accurate determination of the amount of immunogenic HA in the sample. Thus, in methods of the invention, a step of quantifying the immunogenic HA may comprise the use of SRID. However, as mentioned above, SRID has the drawback that it relies on the use of strain-specific antisera which takes weeks or even months to produce. It is therefore preferred that the step of quantifying the immunogenic HA does not comprise the use of SRID.

The invention therefore preferably utilizes quantification methods which do not require the use of strain-specific antisera. Such methods avoid the current bottleneck for influenza vaccine production as they do not require the preparation and calibration of reference antigens every season. Such methods include chromatographic methods like high performance liquid chromatography (HPLC), in particular reverse-phase high performance liquid chromatography (RP-HPLC), but also mass spectrometry methods, like liquid chromatography-mass spectrometry (LC-MS) and liquid chromatography-mass spectrometry/mass spectrometry (LC-MS-MS) and two-dimensional gel electrophoresis (2-DE).

RP-HPLC

RP-HPLC is a form of chromatography which applies a liquid (mobile phase, such as a solvent) to a chromatographic column (stationary phase), with retention on the column depending on the interactions between the stationary phase and components present in a sample. A pump moves the liquid phase through the column and, as conditions change, different molecules can elute from the column at different times. RP-HPLC has a non-polar stationary phase and an aqueous, moderately polar mobile phase. RP HPLC retention times can generally be increased by increasing the proportion of water in the mobile phase (thereby making the affinity of a hydrophobic analyte for a hydrophobic stationary phase stronger relative to the now more hydrophilic mobile phase); conversely they can be decreased by increasing the proportion of non-polar or less-polar organic solvent (e.g., methanol, acetonitrile).

The RP-HPLC column and elution conditions are selected such that the HA1 can be resolved from these other proteins. The ability of RP-HPLC to achieve this resolution is already known from e.g., see reference 11.

Various forms of RP-HPLC are available. Where RP-HPLC is used it can conveniently be performed on a column of 10 μm polystyrenedivinylbenzene (PSDVB) particles with a 4000 Å pore size, but other support materials (e.g., other hydrophobic polymers, such as n alkyl hydrophobic chains of octadecyl, decyl or butyl covalently bonded to silanol groups in silica), particle sizes (e.g., 3-50 μm) and pore sizes (e.g., between 250-5000 Å) can be used, and the properties of PSDVB can be changed by changing the ratio of PS and DVB during copolymerization, or β-derivatisation (e.g., sulfoacylation). Suitable RP-HPLC supports can readily be selected based on their ability to retain and elute HA and to separate it from other materials which are present in a sample. Supports with beads having two pore classes can be used: large "throughpores" which allow convection flow to occur through the particles themselves, quickly carrying sample molecules to short "diffusive" pores inside. This pore arrangement reduces the distance over which diffusion needs to occur and reduces the time required for sample molecules to interact with binding sites. Thus diffusion can be non-limiting and flow rates can be increased (e.g., 1000-5000 cm/hour) without compromising resolution or capacity.

Various elution buffers can be used e.g. using an acetonitrile gradient. Suitable flow rates can readily be selected e.g. between 0.1 and 5 ml/min (e.g., between 0.5 and 1.5 ml/min, or about 0.8 ml/min). Elution can take place at room temperature but elution in the range of 50-70° C. is helpful, e.g., between 55-65° C., or at about 60° C.

The RP-HPLC eluate can be monitored (e.g., for UV absorbance at about 214 nm, or for intrinsic fluorescence using excitation at about 290 nm and emission at about 335 nm) to detect any HA in the sample. The area under the HA peak on a HPLC elution chromatogram can be used to quantify the HA. By using samples of known volume, the amounts of HA determined by these methods can then be used to calculate the HA concentration in the original material from which the sample was taken, e.g., in a bulk antigen preparation, or in an individual vaccine dose. Due to the potential peak overlaps of individual strains, this measurement technique is most reliable for measuring monovalent rather than multivalent vaccine preparations.

Mass Spectrometry

The most preferred method for quantifying HA according to the invention is mass spectrometry (MS), in particular liquid chromatography mass spectrometry (LC-MS) techniques such as liquid chromatography-electrospray ionization-tandem mass spectrometry (LC ESI-MS).

A significant advantage of using LC-MS is that it allows for the specific quantification of proteins in a sample. Furthermore, it allows for the simultaneous measurement of HAs from multiple influenza strains at the same time. This is particularly advantageous where a multivalent influenza vaccine is analyzed as it avoids the need to analyze each HA individually. The methods have the further advantage that they are compatible with the presence of adjuvants, such as MF59 which may interfere with the traditional SRID assay.

Methods for quantifying proteins by mass spectrometry are well known in the art and have been described, for example, in reference 12. These methods general involve an initial step of protease digestion of a denatured sample to provide peptides of the protein that is to be quantified. These peptides are then usually chromatographically separated and then analyzed by MS.

The initial step of analytical proteolysis may be performed using an endoprotease. Suitable endoproteases have been described in reference 13 and include trypsin, chymotrypsin, endoproteinase Asp-N, endoproteinase Arg-C, endoproteinase Glu-C, endoproteinase Lys-C, pepsin, thermolysin, elastase, papain, proteinase K, subtilisin, clostripain, exopeptidase, carboxypeptidase A, B, P, or Y, cathepsin C, acylamino-acid-releasing enzyme, pyroglutamate aminopeptidase, or combinations thereof.

The immunogenic HA is typically digested in an aqueous solution which denatures the HA. The aqueous solution may comprise an inorganic or organic acid. An inorganic acid may be selected from the group consisting of guanidine hydrochloride, nitric acid, phosphoric acid, sulfuric acid, ammonium chloride, ammonium bicarbonate, and combinations thereof. Where an organic acid is used this may be selected from the group consisting of oxalic acid, malonic acid, tartaric acid, acetic acid, formic acid, lactic acid, propionic acid, phthalic acid, benzoic acid, citric acid, succinic acid, salts thereof, and combinations thereof. The exact nature of the acid is not critical as the main purpose of it is to denature the protein to facilitate digestion.

Where the methods of the invention involve a step of protein precipitation, the precipitated protein may be directly resuspended into the buffer used for analytical proteolysis. Alternatively, it may be resuspended into a different buffer and additional components (such as the inorganic or organic acid) may be added later to the resuspended protein.

Following digestion, the reaction may be quenched using known quenching agents such as, for example, trifluoroacetic acid.

Before the obtained peptides are analyzed by MS, labelled surrogate peptides may be added to the reaction mixture. The use of these surrogate peptides has the advantage that they facilitate the quantification of the immunogenic HA as it is not necessary to run a control experiment in parallel. Surrogate peptides therefore can be used as reference peptides (i.e., control) to which fragments of interests are compared for quantitation purposes. Typically, surrogate peptides are synthetic polypeptides of predetermined amino acid sequences. Any suitable surrogate peptide may be used as a reference, which provides a known shift in its mass such that it can be detected with ease. For example, a surrogate peptide may include one or more chemical moiety or moieties of known mass in addition to the core amino acid stretch. In some embodiments, a surrogate peptide may contain one or more modified amino acids such that they have slightly different masses as compared to their natural counterparts. In some embodiments, surrogate peptides may be isotopically labelled. Preferably, the isotope label is selected from the list consisting of $^{15}N$ and $^{13}C$.

Methods for preparing surrogate peptides are well known in the art. These surrogate peptides are preferably chosen so that they have a good retention time on the liquid chromatography (LC), have acceptable ionization efficiency on the ESI, and are free from potential post-translational modifications (such as N-linked glycans and methionine).

Where the quantity of more than one influenza antigen is assessed, several strain-specific surrogate peptides may be added. For example, where a sample comprises antigens from n influenza strains, n types of strain-specific surrogate peptides can be added. The number of strain-specific surrogate peptides may also differ from the number of antigens from different strains in the sample. For example, a skilled person may wish to analyze only two antigens in a quadrivalent sample.

Suitable labels for the surrogate peptides include fluorine, a fluorescent label, such as rhodamine, Oregon green or others known in the art, radioactive labels, mass labels (ref. 13). A calibration curve is optionally used and represents a mathematical relationship between a known amount of at least one immunogenic antigen fragment peptide and a ratio; wherein the ratio is the quotient of the known amount of the at least one peptide and a constant amount of at least one standard peptide.

The sample may be analyzed using liquid chromatography (LC) followed by a step of mass spectrometry (MS). Suitable LC methods are known to a skilled person and include high performance LC (HPLC), ultra-high performance LC (UPLC), and standard column or slab gel chromatography techniques. Preferably, the peptides are separated using UPLC.

Following chromatography, the peptides may be detected using mass spectrometry. This has the advantage that it allows the specific detection of the peptides of interest and thus provides a more accurate quantification. In particular, the eluate from chromatography columns often contains contaminants and adding a step of MS avoids the over-quantification of the immunogenic HA in the sample due to these contaminants.

The methods of the invention may be practiced using any MS technique. Suitable detection and quantitation systems include electrospray, matrix assisted laser desorbtion ionization (MALDI), time of flight (TOF), multiple quadrupole, and other types of mass spectrometry systems known in the art. Illustratively, a Waters Q-Tof Premier TOF quadrupole tandem mass spectrometer available from Waters, Corp. or an API 4000-Q trap triple quadrupole tandem mass spectrometer (Applied Biosystems, Foster City, Calif.) are each suitable for use in the present invention.

A particularly preferred method for quantifying immunogenic HA according to the invention is the liquid chromatography selected reaction monitoring (LC-SRM) assay (ref. 14).

Modified Single-Radial Immunodiffusion (SRID) Assay

As described above, protease digestion of antigen samples selectively degrades inactive forms of antigens, so that an otherwise conformationally insensitive biophysical quantification technique, such as reversed-phase high pressure liquid chromatography (RP-HPLC), can be used to specifically quantify protease-resistant, immunologically active antigens (also see Examples below). Based in part on the recognition that protease can be used to selectively degrade undesirable forms of antigens, the invention in another aspect provides "modified" SRID assay that achieves improved accuracy.

According to this aspect of the invention, biological proteolysis (e.g., protease digestion) can be incorporated into the otherwise standard SRID protocol to achieve more accurate assay results. As detailed in the Examples below, trypsin digestion can improve the specificity of SRID so that it can quantify immunologically active, pre-fusion HA when it is mixed with immunologically inactive, post-fusion HA. The SRID assay, which remains the standard in vitro potency assay in the field, is believed to specifically detect immunologically active HA. As demonstrated in the Examples, with conformationally homogeneous HA preparations, the SRID assay can be used to specifically detect native, pre-fusion HA, which elicit influenza neutralizing and hemagglutination inhibiting antibodies in mice, and it does not detect low-pH stressed, post-fusion HA, which was selectively removed from the SRID gel during a blotting step and was not immunologically active. Work disclosed herein has surprisingly revealed that this selective detection is due to the SRID format itself, but not due to conformational specificity of the sheep antiserum used in the SRID, as the same antiserum can detect non-stressed and low-pH-stressed HA similarly when used in an ELISA format. However, when low-pH stressed HA is mixed with non-stressed HA, SRID can detect both forms, leading to over-quantification of immunologically active HA.

Accordingly, the invention provides methods and intermediates drawn to an improved SRID assay. The invention thus includes a method comprising a step of subjecting a sample containing HA to biological proteolysis (e.g., trypsin digestion) prior to quantifying HA by SRID. The invention further includes use of a sample, which has been subjected to biological proteolysis (as defined herein), in carrying out SRID assay (e.g., to quantify the immunogenic HA in the sample).

Sample

The sample is usually an influenza vaccine or a vaccine bulk antigen preparation. This can either be a sample obtained from a bulk vaccine or a unit dose of a vaccine albeit the methods will usually be performed on the bulk vaccine as the quantification is used to ensure that a full HA dose (usually 15 µg per strain for an adult dose of a seasonal influenza vaccine) is present in dose volume of the vaccine (usually 0.5 mL).

The methods of the invention can be performed on bulk vaccines or on the final vaccine. They may also be performed on intermediate products found during the production process.

Tests on the final vaccine may be performed to ensure that an accurate amount of immunogenic HA is present. The methods of the invention may also be performed on bulk vaccines to ensure that the correct amount of immunogenic HA is added to the final vaccine. The bulk or the vaccine may be monovalent. It may also be multivalent, for example following mixing of two, three, four, five or six monobulks. As seasonal influenza vaccines are typically trivalent or quadrivalent, the multivalent bulk or the vaccine will usually be trivalent or quadrivalent. The methods of the invention may be performed before or after sterile filtration of the bulk or the vaccine. They may further be performed before or after addition of an adjuvant. Where the sample is a vaccine, the methods may be performed before or after packaging.

It can also be useful to perform the methods of the invention on bulk vaccines (monovalent or multivalent) or vaccines which have been stored. The bulk or vaccine may have been stored at a temperature below 10° C. (for example 4° C.) or below 0° C. (for example −20° C.), for example for a period of more than 1 week, more than 2 weeks, more than 3 weeks, more than 4 weeks etc. It is possible that storage results in conformational changes in the HA from the immunogenic state to the inactive HA. By performing the methods of the invention on samples which have been stored, it can be ensured that accurate amounts of immunogenic HA are found in the final vaccine. The methods of the invention also allow for the shelf-life of a sample to be assessed. In particular, a sample may be stored and fractions of the sample may be tested at several time points for the amount of immunogenic HA using the methods of the invention to assess at which point the amount of immunogenic HA drops. The higher the stability of the sample, the longer it will take for the amount of immunogenic HA to decrease significantly. Samples where this takes longer will be considered to have a higher stability.

Various forms of influenza virus vaccine are currently available, and vaccines are generally based either on live virus or on inactivated virus. Inactivated vaccines may be based on whole virions, split virions, or on purified surface antigens. Influenza antigens can also be presented in the form of virosomes or can be expressed in a recombinant host (e.g., in an insect cell line using a baculovirus vector) and used in purified form (ref. 15). The invention can be used with any of these types of vaccine, but will typically be used with inactivated vaccines.

The antigen may take the form of a whole attenuated virus or an inactivated virus. Chemical means for inactivating a virus include treatment with an effective amount of an inactivation agent, such as one or more of the following agents: detergents, formaldehyde, peroxides, formalin, beta propiolactone, or UV light. Beta-propiolactone has the advantage that it can be easily removed from the preparation and this agent is therefore preferred. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. The INFLEXAL™ product is a whole virion inactivated vaccine.

Where an inactivated virus is used, the vaccine may comprise whole virion, split virion, or purified surface antigens (including hemagglutinin and, usually, also including neuraminidase).

Virions can be harvested from virus containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating virions with detergents (e.g., ethyl ether, polysorbate 80, deoxycholate, tri N-butyl phosphate, Triton X-100, Triton N101, cetyltrimethylammonium bromide, etc.) to produce subvirion preparations, including the Tween-ether' splitting process. Methods of splitting influenza viruses are well known in the art, e.g., see refs. 16-21, etc. Splitting of the virus is typically carried out by disrupting or fragmenting whole virus, whether infectious or non-infectious with a disrupting concentration of a splitting agent. The disruption results in a full or partial solubilization of the virus proteins, altering the integrity of the virus. Preferred splitting agents are non-ionic and ionic (e.g., cationic) surfactants, e.g., alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g., the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g., in a sucrose density gradient solution). Split virions can usefully be resuspended in sodium phosphate-buffered isotonic sodium chloride solution. The AFLURIA™, BEGRIVAC™, FLUARIX™, FLUZONE™ and FLUSHIELD™ products are split vaccines.

Purified surface antigen vaccines comprise the influenza surface antigens HA and, typically, also neuraminidase. Processes for preparing these proteins in purified form are well known in the art. The FLUVIRIN™, AGRIPPAL™, FLUAD™, FLUCELVAX™, and INFLUVAC™ products are subunit vaccines.

Influenza antigens can also be presented in the form of virosomes (ref. 22) (nucleic acid free viral-like liposomal particles), as in the INFLEXAL V™ and INVAVAC™ products.

The invention can also be used with recombinant influenza vaccines. An example of such a vaccine is Flublok™.

The influenza virus may be attenuated. The influenza virus may be temperature-sensitive. The influenza virus may be cold adapted. These three possibilities apply in particular for live viruses.

Influenza virus strains for use in vaccines change from season to season. In the current inter-pandemic period, vaccines typically include two influenza A strains (H1N1 and H3N2) and one or two influenza B strain, and trivalent or quadrivalent vaccines are typical. The invention can be use with these vaccines. It is also useful for viruses from pandemic strains (i.e., strains to which the vaccine recipient 5 and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may be used with vaccines that protect against one or more of influenza A virus hemagglutinin subtypes H1, H2, H3, H4, H5, H6, H7, H8, H9, H10, H11, H12, H13, H14, H15 or H16. The invention may be used with vaccines that protect against one or more of influenza A virus NA subtypes N1, N2, N3, N4, N5, N6, N7, N8 or N9.

Other strains that can usefully be included in vaccine compositions are strains which are resistant to antiviral therapy (e.g., resistant to oseltamivir (ref. 23) and/or zanamivir), including resistant pandemic strains (ref. 24).

As discussed above, HA can undergo a transition to post-fusion state during the vaccine production process either due to natural stability limitations or due to manufacturing steps necessary when producing the vaccine (such as inactivation). The invention may be practiced with samples in which at least 60%, at least 65%, at least 70%, at least 75%, 80%, at least 85%; at least 90%, at least 95%, or at least 99% of HA in the sample is in an active/immunogenic (pre-fusion) form and/or in which less than 20%, 15%, 10%, 5% or 1% of HA in the sample is in an inactive (post-fusion)

form. The ratio of active to inactive HA in the sample may be at least 4:1, 10:1, 20:1, 50:1 or 100:1.

Generally, it is useful for the sample to contain equal to or more than 30 µg/mL of active HA per strain as a standard adult dose of the influenza vaccine requires 15 µg HA per 0.5 mL of the antigen per strain. Having a sample with a HA concentration of ≥30 µg/mL of active HA per strain makes the vaccine production process easier as the antigen does not need to be concentrated to provide a human dose. Samples with a concentration of less than 30 µg/mL of active HA per strain may also be used, for example at least 25 µg/mL of active HA per strain, 20 µg/mL of active HA per strain, at least 15 µg/mL of active HA per strain, at least 10 µg/mL of active HA per strain etc. In this case, the final vaccine may have a larger dose volume to accommodate a final amount of 15 µg HA per dose, the antigen may be concentrated using standard methods in the art or the final vaccine may contain a lower amount of HA. A lower amount of HA may be used for pandemic influenza vaccines, for example, in which case the vaccine may be adjuvanted. The sample may contain less than 4 µg, 3 µg, 2 µg, 1 µg, 0.5 µg or 0.25 µg of inactive HA.

The final vaccine product may contain no more than 15 µg of total HA per strain per dose, e.g., no more than 14 µg, no more than 13 µg, no more than 12 µg, no more than 11 µg, no more than 10 µg, no more than 9 µg, no more than 8 µg, no more than 7 µg, no more than 6 µg, no more than 5 pg of total HA per strain. In some embodiments, the total HA in such a product, at least 50% of the antigen is in immunogenic forms, e.g., at least 60%, at least 70%, at least 80%, at least 90%. In some embodiments, no more than 50% of the total HA contained in a final vaccine product is in trypsin-sensitive forms, e.g., no more than 40%, no more than 30%, no more than 20%, no more than 10% of the total HA.

The viruses used as the source of the antigens can be grown either on eggs or on cell culture. The current standard method for influenza virus growth uses embryonated hen eggs, which may be specific pathogen-free, with virus being purified from the egg contents (allantoic fluid). More recently, however, viruses have been grown in animal cell culture and, for reasons of speed and patient allergies, this growth method is preferred. If egg-based viral growth is used then one or more amino acids and/or steroids may be introduced into the allantoid fluid of the egg together with the virus (ref. 25).

When cell culture is used, the viral growth substrate will typically be eukaryotic cells, such as a cell line of mammalian origin. Suitable mammalian cells include, but are not limited to, hamster, cattle, primate (including humans and monkeys) and dog cells. Various cell types may be used, such as fibroblasts and epithelial cells. Non-limiting examples of suitable cell types include kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells (refs. 26-29), derived from Madin Darby canine kidney; Vero cells (refs. 30-32), derived from African green monkey (*Cercopithecus aethiops*) kidney; or PER.C6 cells (ref. 33), derived from human embryonic retinoblasts. These cell lines are widely available e.g. from the American Type Cell Culture (ATCC) collection (ref. 34), from the Coriell Cell Repositories (ref. 35), or from the European Collection of Cell Cultures (ECACC). For example, the ATCC supplies various different Vero cells under catalog numbers CCL 81, CCL 81.2, CRL 1586 and CRL-1587, and it supplies MDCK cells under catalog number CCL 34. PER.C6 is available from the ECACC under deposit number 96022940.

Influenza viruses can also be grown on avian cells lines (e.g., refs. 36-38), including avian embryonic stem cells (refs. 36 & 39) and cell lines derived from ducks (e.g., duck retina), or from hens. Suitable avian embryonic stem cells include the EBx cell line derived from chicken embryonic stem cells, EB45, EB14, and EB14-074 (ref. 40). Chicken embryo fibroblasts (CEF) can also be used. The most preferred avian cell line is the EB66 cell line, which is derived from duck embryonic stem cells. This cell line has been reported to work well for producing influenza antigens (ref. 41).

The most preferred cell lines for growing influenza viruses are MDCK cells. The original MDCK cell line is available from the ATCC as CCL 34, but derivatives of this cell line may also be used. For instance, reference 26 discloses a MDCK cell line that was adapted for growth in suspension culture ('MDCK 33016', deposited as DSM ACC 2219). Similarly, reference 42 discloses a MDCK-derived cell line that grows in suspension in serum free culture ('B-702', deposited as FERM BP-7449). Reference 43 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 44 discloses MDCK cell lines with high susceptibility to infection, including 'MDCK.5F1' cells (ATCC CRL 12042). Any of these MDCK cell lines can be used.

Where virus has been grown on a cell line then the composition will advantageously be free from egg proteins (e.g., ovalbumin and ovomucoid) and from chicken DNA, thereby reducing allergenicity.

Where virus has been grown on a cell line then the culture for growth, and also the viral inoculum used to start the culture, will preferably be free from (i.e., will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses (in particular porcine circoviruses), and/or parvoviruses (ref. 45). Absence of herpes simplex viruses is particularly preferred.

Where virus has been grown on a cell line then the composition preferably contains less than 10 ng (preferably less than 1 ng, and more preferably less than 100 pg) of residual host cell DNA per dose (typically 0.25 mL for children or 0.5 mL for adults), although trace amounts of host cell DNA may be present. In general, the host cell DNA that it is desirable to exclude from compositions of the invention is DNA that is longer than 100 bp.

Measurement of residual host cell DNA is now a routine regulatory requirement for biologicals and is within the normal capabilities of the skilled person. The assay used to measure DNA will typically be a validated assay (refs. 46 & 47). The performance characteristics of a validated assay can be described in mathematical and quantifiable terms, and its possible sources of error will have been identified. The assay will generally have been tested for characteristics such as accuracy, precision, specificity. Once an assay has been calibrated (e.g., against known standard quantities of host cell DNA) and tested then quantitative DNA measurements can be routinely performed. Three principle techniques for DNA quantification can be used: hybridization methods, such as Southern blots or slot blots (ref. 48); immunoassay methods, such as the Threshold™ System (ref. 49); and quantitative PCR (ref. 50). These methods are all familiar to the skilled person, although the precise characteristics of each method may depend on the host cell in question, e.g., the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals (ref. 49). A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™ Althea Technologies, etc. A comparison of a chemiluminescent hybridisation assay and the total DNA Threshold™ system for measuring host cell DNA contamination of a human viral vaccine can be found in reference 51.

Contaminating DNA can be removed during vaccine preparation using standard purification procedures, e.g., chromatography, etc. Removal of residual host cell DNA can be enhanced by nuclease treatment e.g. by using a DNase. A convenient method for reducing host cell DNA contamination is disclosed in references 52 & 53, involving a two-step treatment, first using a DNase (e.g., Benzonase), which may be used during viral growth, and then a cationic detergent (e.g., CTAB), which may be used during virion disruption. Treatment with an alkylating agent, such as β-propiolactone, can also be used to remove host cell DNA, and advantageously may also be used to inactivate virions (ref. 54). Methods using two steps of treatment with an alkylating agent or a combination of a DNase and an alkylating agent have also been described (ref. 55).

Vaccines containing no more than 10 ng of residual host cell DNA per dosage are preferred. For example, vaccines containing <10 ng (e.g., <1 ng, <100 pg) host cell DNA per 15 μg of hemagglutinin are preferred, as are vaccines containing <10 ng (e.g., <1 ng, <100 pg) host cell DNA per 0.25 ml volume. Vaccines containing <10 ng (e.g., <1 ng, <100 pg) host cell DNA per 50 μg of hemagglutinin are more preferred, as are vaccines containing <10 ng (e.g., <1 ng, <100 pg) host cell DNA per 0.5 ml volume.

It is preferred that the average length of any residual host cell DNA is less than 500 bp, e.g., less than 400 bp, less than 300 bp, less than 200 bp, less than 100 bp, etc.

For growth on a cell line, such as on MDCK cells, virus may be grown on cells in suspension (refs. 26, 56 & 57) or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. (ref. 58) (e.g., 30 36° C., or at about 30° C., 31° C., 32° C., 33° C., 34° C., 35° C., 36° C.), for example during viral replication.

The method for propagating virus in cultured cells generally includes the steps of inoculating the cultured cells with the strain to be cultured, cultivating the infected cells for a desired time period for virus propagation, such as for example as determined by virus titer or antigen expression (e.g., between 24 and 168 hours after inoculation) and collecting the propagated virus. The cultured cells are inoculated with a virus (measured by PFU or $TCID_{50}$) to cell ratio of 1:1000 to 1:1, 1:500 to 1:1, 1:100 to 1:5, or 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g., monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at an m.o.i of about 0.01. Infected cells may be harvested 30 to 60 hours post infection. Preferably, the cells are harvested 34 to 48 hours post infection, for example 38 to 40 hours post infection. Proteases (typically trypsin) are generally added during cell culture to allow viral release, and the proteases can be added at any suitable stage during the culture.

The influenza virus may be a reassortant strain, and may have been obtained by reverse genetics techniques. Reverse genetics techniques (e.g., refs. 59-63) allow influenza viruses with desired genome segments to be prepared in vitro using plasmids or linear expression constructs. Typically, it involves expressing (a) DNA molecules that encode desired viral RNA molecules e.g. from poII promoters, and (b) DNA molecules that encode viral proteins e.g. from poIII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred (refs. 64-66), and these methods will also involve the use of plasmids to express all or some (e.g., just the PB1, PB2, PA and NP proteins) of the viral proteins, with 12 plasmids being used in some methods. The use of linear expression constructs is also possible (ref. 67).

To reduce the number of plasmids needed, a recent approach (ref. 68) combines a plurality of RNA polymerase I transcription cassettes (for viral RNA synthesis) on the same plasmid (e.g., sequences encoding 1, 2, 3, 4, 5, 6, 7 or all 8 influenza A vRNA segments), and a plurality of protein coding regions with RNA polymerase II promoters on another plasmid (e.g., sequences encoding 1, 2, 3, 4, 5, 6, 7 or all 8 influenza A mRNA transcripts). Preferred aspects of the reference 68 method involve: (a) PB1, PB2 and PA mRNA encoding regions on a single plasmid; and (b) all 8 vRNA encoding segments on a single plasmid. Including the NA and HA segments on one plasmid and the six other segments on another plasmid can also facilitate matters.

As an alternative to using poII promoters to encode the viral RNA segments, it is possible to use bacteriophage polymerase promoters (ref. 69). For instance, promoters for the SP6, T3 or T7 polymerases can conveniently be used.

Because of the species specificity of polI promoters, bacteriophage polymerase promoters can be more convenient for many cell types (e.g., MDCK), although a cell must also be transfected with a plasmid encoding the exogenous polymerase enzyme.

In other techniques it is possible to use dual polI and polIII promoters to simultaneously code for the viral RNAs and for expressible mRNAs from a single template (refs. 70 & 71).

Thus an influenza A virus may include one or more RNA segments from a A/PR/8/34 virus (typically 6 segments from A/PR/8/34, with the HA and NA segments being from a vaccine strain, i.e. a 6:2 reassortant), particularly when viruses are grown in eggs. It may also include one or more RNA segments from a A/WSN/33 virus, or from any other virus strain useful for generating reassortant viruses for vaccine preparation. References 72 and 73 also discuss suitable backbones for reassorting influenza A and B strains.

Typically, the invention protects against a strain that is capable of human-to-human transmission, and so the strain's genome will usually include at least one RNA segment that originated in a mammalian (e.g., in a human) influenza virus. It may include an NS segment that originated in an avian influenza virus.

Hemagglutinin (HA) is the main immunogen in inactivated influenza vaccines, and vaccine doses are standardised by reference to HA levels, typically as measured by a single radial immunodiffusion (SRID) assay. Vaccines typically contain about 15 μg of HA per strain, although lower doses are also used e.g. for children, or in pandemic situations. Fractional doses such as ½ (i.e., 7.5 μg HA per strain), ¼ and ⅛ have been used (refs. 74 & 75), as have higher doses (e.g., 3× or 9× doses (refs. 76 & 77)). Thus vaccines may include between 0.1 and 150 μg of HA per influenza strain, preferably between 0.1 and 50 μg, e.g., 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 1.9, about 1.5, etc. per strain. These lower doses are most useful when an adjuvant is present in the vaccine, as with the invention. The components of the vaccines, kits and processes of the invention (e.g., their volumes and concentrations) may be selected to provide these antigen doses in final products.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

HA used with the invention may be a natural HA as found in a virus, or may have been modified. For instance, it is known to modify HA to remove determinants (e.g., polybasic regions around the cleavage site between HA1 and HA2) that cause a virus to be highly pathogenic in avian and other species, as these determinants can otherwise prevent a virus from being grown in eggs.

Compositions may include detergent e.g. a polyoxyethylene sorbitan ester surfactant (known as 'Tweens'), an octoxynol (such as octoxynol-9 (Triton X-100) or t octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol 10, α-tocopheryl hydrogen succinate and polysorbate 80. Other residual components in trace amounts could be antibiotics (e.g., neomycin, kanamycin, polymyxin B).

An inactivated but non whole cell vaccine (e.g., a split virus vaccine or a purified surface antigen vaccine) may include matrix protein, in order to benefit from the additional T cell epitopes that are located within this antigen. Thus a non-whole cell vaccine (particularly a split vaccine) that includes hemagglutinin and neuraminidase may additionally include M1 and/or M2 matrix protein. Where a matrix protein is present, inclusion of detectable levels of M1 matrix protein is preferred. Nucleoprotein may also be present.

The antigen in the sample will typically be prepared from influenza virions but, as an alternative, antigens such as hemagglutinin can be expressed in a recombinant host (e.g., in yeast using a plasmid expression system, or in an insect cell line using a baculovirus vector) and used in purified form (refs. 78 & 79). In general, however, antigens will be from virions.

The sample may have been, or may be suspected to have been exposed to a stress condition. The methods of the invention may be used to ensure that an accurate amount of immunogenic HA is present in the sample, when the sample has been exposed to one or more of a range of stress conditions. In some embodiments, the stress condition is selected from pH below 6.5, freeze-and-thaw and vortexing. In some embodiments, the stress condition is selected from pH below 6.5, freeze-and-thaw and vortexing and the quantification is performed using RP-HPLC, as described herein. In some embodiments, the stress condition is selected from pH below 6.5, a pH above 7.5, a temperature above 50° C., or freeze-and-thaw. In some embodiments, the stress condition is selected from pH below 6.5, a pH above 7.5, a temperature above 50° C., or freeze-and-thaw and the quantification is performed using mass spectrometry, as described herein. The mass spectrometry method may be a method as described herein wherein the separation step (e.g. precipitation) is dispensed with. A pH below 6.5 includes a pH of 4 to 6 (e.g. between pH 4.0 and pH 6.0). Freeze-and-thaw may be in PBS buffer. Freeze-and-thaw may be in Tris buffer. In preferred embodiments, the stress condition is pH below 6.5 (e.g. pH 4 to pH 6). Preferably, the sample contains, or is suspected to contain inactive HA (e.g. post-fusion HA).

Pharmaceutical Compositions

Vaccines prepared according to the invention are pharmaceutically acceptable. They may include components in addition to the antigen and adjuvant, e.g., they will typically include one or more pharmaceutical carrier(s) and/or excipient(s). A thorough discussion of such components is available in reference 80. The carrier(s)/excipient(s) used in mucosal vaccines may be the same as or different from those used in parenteral vaccines.

Compositions may include preservatives such as thiomersal or 2-phenoxyethanol. It is preferred, however, that the vaccines should be substantially free from (i.e., less than 5 μg/ml) mercurial material e.g. thiomersal-free (refs. 20 & 81). Vaccines containing no mercury are more preferred.

To control tonicity, particularly in injectable vaccines, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions for injection will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination (ref. 82), but keeping osmolality in this range is nevertheless preferred.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition will generally be between 5.0 and 8.1, and more typically between 6.0 and 8.0, e.g., between 6.5 and 7.5, or between 7.0 and 7.8. A process of the invention may therefore include a step of adjusting the pH of the bulk vaccine prior to packaging.

The composition is preferably sterile. The composition is preferably non pyrogenic, e.g., containing <1 EU (endotoxin unit, a standard measure) per dose, and preferably <0.1 EU per dose. The composition is preferably gluten free.

The composition may include material for a single immunization, or may include material for multiple immunizations (i.e., a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e., about 0.25 ml) may be administered to children. For intranasal administration, this total dosage volume can be split between nostrils, e.g., ½ in each nostril.

Compositions and kits are preferably stored at between 2° C. and 8° C. They should not be frozen. They should ideally be kept out of direct light.

Adjuvants

One of the advantages of the methods of the invention is that they allow HA quantification of immunogenic HA in adjuvanted influenza vaccines. Thus the sample which is used in the methods of the invention may be an adjuvanted influenza vaccine. The adjuvant is preferably an oil-in-water emulsion adjuvant as they have been shown to work well with influenza antigens.

Oil-in-water Emulsion Adjuvants

Oil-in-water emulsions have been found to be particularly suitable for use in adjuvanting influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with an average size less than 220 nm are preferred as they can be subjected to filter sterilization.

In preferred embodiments, the oil-in-water emulsion is uniform. A uniform emulsion is characterized in that a majority of droplets (particles) dispersed therein is within a specified size range (e.g., in diameter). Suitable specified size range can be, for example, between 50-220 nm, between 50-180 nm, between 80-180 nm, between 100-175 nm, between 120-185 nm, between 130-190 nm, between 135-175 nm, between 150-175 nm. In some embodiments, the uniform emulsion contains ≤10% of the number of droplets (particles) that are outside of the specified range of diameters. In some embodiments, mean particle size of oil droplets in the oil-in-water emulsion preparation is between 135-175 nm, e.g., 155 nm±20 nm as measured by dynamic light scattering, and such a preparation contains not more than $1 \times 10^7$ large particles per mL of the preparation, as measured by optical particle sensing. "Large particles" as used herein mean those having diameters >1.2 μm, typically between 1.2-400 μm. In preferred embodiments, the uniform emulsion contains less than 10%, less than 5%, or less than 3% of the droplets that fall outside of the preferred size range. In some embodiments, the mean droplet size of particles in an oil-in-water emulsion preparation is between 125-185 nm, e.g., about 130 nm, about 140 nm, about 150 nm, about 155 nm, about 160 nm, about 170 nm, or about 180 nm, and the oil-in-water emulsion is uniform in that less than 5% of the number of droplets in the preparation fall outside the 125-185 nm range.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used, e.g., Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

The most preferred oil-in-water emulsions are squalene-in-water emulsions, preferably submicron squalene-in-water emulsions.

Specific oil-in-water emulsions useful with the invention include, but are not limited to, the following, from which squalene-containing emulsions are preferred:

A submicron emulsion of squalene, polysorbate 80, and sorbitan trioleate. The emulsion may include citrate ions in the aqueous phase, e.g., 10 mM sodium citrate buffer. The emulsion may comprise 3.2-4.6 mg/ml squalene, 4.1-5.3 mg/ml polysorbate 80, and 4.1-5.3 mg/ml sorbitan trioleate. The composition of the emulsion by volume can be about 4.6% squalene, about 0.45% polysorbate 80 and about 0.5% sorbitan trioleate. The adjuvant known as "MF59" (refs. 83-85) is described in more detail in Chapter 10 of reference 86 and chapter 12 of reference 87. Squalene, polysorbate 80 and sorbitan trioleate may be present at a weight ratio of 9750:1175:1175. Concentrations of about 39 mg/mL squalene, about 4.7 mg/mL polysorbate 80, and about 4.7 mg/mL sorbitan trioleate are typical. A Z-average droplet size of between 155-185 nm is preferred, with a polydispersity of <0.2.

An emulsion comprising squalene, a tocopherol (in particular, DL-α-tocopherol), and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g., 0.90) as this can provide a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ("AS03") includes 4.3% by weight squalene, 4.8% by weight tocopherol, and 2% by weight polysorbate 80. Concentrations of about 42.7 mg/mL squalene, about 47.4 mg/mL DL-α-tocopherol, and about 19.4 mg/mL polysorbate 80 are typical. A Z-average droplet size of between 140-170 nm is preferred. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 (ref. 88), e.g., in the ratios discussed above.

An emulsion comprising squalene, an aqueous solvent, a polyoxyethylene alkyl ether hydrophilic nonionic surfactant (e.g., polyoxyethylene (12) cetostearyl ether) and a hydrophobic nonionic surfactant (e.g., a sorbitan ester or mannide ester, such as sorbitan monooleate or 'Span 80'). The emulsion is preferably thermoreversible and/or has at least 90% of the oil droplets (by volume) with a size less than 200 nm (ref. 89). The emulsion may also include one or more of: alditol; a cryoprotective agent (e.g. a sugar, such as dodecylmaltoside and/or sucrose); and/or an alkylpolyglycoside. The emulsion may include a TLR4 agonist (ref. 90). Such emulsions may be lyophilized. A preferred emulsion includes squalene, sorbitan oleate, polyoxyethylene cetostearyl ether and mannitol (e.g., 32.5% squalene, 4.82% sorbitan oleate, 6.18% polyoxyethylene cetostearyl ether and 6% mannitol; % s by weight), with an average droplet size below 150 nm. Concentrations of about 49.6 mg/mL squalene, about 7.6 mg/mL sorbitan oleate, and about 9.6 mg/mL polyoxyethylene cetostearyl ether, and 9.2 mg/mL mannitol are typical.

An emulsion comprising squalene, phosphatidylcholine, poloxamer 188, glycerol and an ammonium phosphate buffer (ref. 91), optionally also including an α-tocopherol ('SE').

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g., polysorbate 80), a Triton detergent (e.g., Triton X-100) and a tocopherol (e.g., an α-tocopherol succinate). The emulsion may include these three components at a mass ratio of about 75:11:10 (e.g., 750 µg/ml polysorbate 80, 110 µg/ml Triton X-100 and 100 µg/ml α-tocopherol succinate), and these concentrations should include any contribution of these components from antigens. The emulsion may also include squalene. The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (ref. 92) (0.05-1% Thr-MDP, 5% squalane, 2.5% Pluronic L121 and 0.2% polysorbate 80). It can also be used without the Thr-MDP, as in the "AF" adjuvant (ref. 93) (5% squalane, 1.25% Pluronic L121 and 0.2% polysorbate 80). Microfluidisation is preferred.

An emulsion of squalene, poloxamer 105 and Abil-Care (ref. 94). The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% oil, 0.1-10% phospholipid, and 0.05-5% non-ionic surfactant. As described in reference 95, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolizable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 96, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion in which a saponin (e.g., QuilA or QS21) and a sterol (e.g., a cholesterol) are associated as helical micelles (ref. 97).

An emulsion comprising a mineral oil, a non-ionic lipophilic ethoxylated fatty alcohol, and a non-ionic hydrophilic surfactant (e.g., an ethoxylated fatty alcohol and/or polyoxyethylene-polyoxypropylene block copolymer) (ref. 98).

An emulsion comprising a mineral oil, a non-ionic hydrophilic ethoxylated fatty alcohol, and a non-ionic lipophilic surfactant (e.g., an ethoxylated fatty alcohol and/or polyoxyethylene-polyoxypropylene block copolymer) (ref. 98).

To make a vaccine for injection these emulsions will generally be mixed with an aqueous immunogen preparation. This mixing typically involves the emulsion in aqueous form with the immunogen in aqueous form at a 1:1 volume ratio, in which case the proportion of the emulsion's components will be halved in a final vaccine. For instance, an emulsion with 5% by volume squalene can be mixed at a 1:1 ratio with an antigen solution to give a vaccine with a final concentration of 2.5% by volume. Other mixing ratios are, of course, possible e.g. using a volume ratio of the two liquids for mixing between 5:1 and 1:5. Thus in a vaccine composition the concentrations of components of the emulsions noted above may be modified by dilution (e.g., by an integer, such as 2 or 3) in which their ratios stay the same. For example, pediatric vaccines may contain lower concentrations of an adjuvant, e.g., 4%, 3.5%, 3%, 2.5%, 2%, 1.5%, or 1% by volume squalene.

After the antigen and adjuvant have been mixed, hemagglutinin antigen will generally remain in aqueous solution but may distribute itself around the oil/water interface. In general, little if any hemagglutinin will enter the oil phase of the emulsion.

Where a composition includes a tocopherol, any of the α, β, γ, δ, ε or ξ tocopherols can be used, but α-tocopherols are preferred. The tocopherol can take several forms, e.g., different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g., aged 60 years or older) because vitamin E has been reported to have a positive effect on the immune response in this patient group (ref. 99). They also have antioxidant properties that may help to stabilize the emulsions (ref. 100). A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds (ref. 20). Preservative-free vaccines are particularly preferred.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x+10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal derived materials.

It will be understood that the invention has been described by way of example only and modifications may be made whilst remaining within the scope and spirit of the invention. The invention encompasses the following non-limiting embodiments:

1) A method comprising the steps of: (a) providing a sample comprising immunogenic HA, inactive HA, or combination thereof; (b) subjecting the sample to biological proteolysis, wherein the inactive HA is digested and the immunogenic HA remains undigested; (c) separating the digested inactive HA from the undigested immunogenic HA in the sample; (d) subjecting the undigested immunogenic HA to analytical proteolysis, so as to provide fragments of digested immunogenic HA; and, (e) carrying out a liquid chromatography-electrospray ionization-tandem mass spectrometry (LC-ESI-MS) in the presence of at least one labeled reference HA peptide, to quantify the amount of immunogenic HA in the sample.

2) A method comprising the steps of: (a) providing a sample comprising immunogenic HA, inactive HA, or combination thereof; (b) subjecting the sample to biological proteolysis by one or more proteases, wherein the inactive HA is digested and the immunogenic HA remains undigested; (c) subjecting the mixture of undigested immunogenic HA and digested inactive HA to analytical proteolysis using one or more proteases, wherein the analytical proteolysis cannot cleave the immunogenic HA at one or more cleavage site(s) which can be cleaved in the inactive HA during biological proteolysis, so as to provide fragments of digested immunogenic HA that comprise immunogenic HA-derived peptide(s) that is/are distinguishable from the inactive HA-derived peptides; and, (d) carrying out liquid chromatography-electrospray ionization-tandem mass spectrometry (LC-ESI-MS) in the presence of at least one labeled reference HA peptide, to quantify the amount of immunogenic HA in the sample.

3) The method of embodiment 1, wherein the undigested immunogenic HA of step (d) is in a stressed form.

4) The method of embodiment 3, wherein the stressed form of undigested immunogenic HA is obtained by exposure to a pH below 6.5, a pH above 7.5, a temperature above 50° C.; or freeze-and-thaw.

5) The method of embodiment 4, wherein the low pH is below pH 6.0.

6) The method of embodiment 5, wherein the low pH is between pH 4.0 and 6.0.

7) The method of any preceding embodiment, wherein the analytical proteolysis step comprises digestion with a serine protease under conditions sufficient to generate fragments of the immunogenic HA.

8) The method of embodiment 7, wherein the analytical proteolysis is performed at about 37° C. for up to 18 hours.

9) The method of any preceding embodiment, as dependent on embodiment 1, wherein the protease in step (b) and the protease in step (d) are the same, or different.

10) A method for quantifying immunogenic influenza HA in a sample, comprising the steps of: subjecting the sample to biological proteolysis; separating the immunogenic HA from other components in the sample; and, quantifying the immunogenic HA in the sample.

11) The method of any preceding embodiment, as dependent on embodiment 1, wherein the biological proteolysis comprises proteolysis with a protease.
12) The method of embodiment 11, wherein the protease is a serine protease.
13) The method of embodiment 12, wherein the serine protease is trypsin.
14) The method of any preceding embodiment, wherein the biological proteolysis is carried out at 37° C.
15) The method of any one of embodiments 10-14, wherein the biological proteolysis is carried out for 30 minutes, 60 minutes, 90 minutes or 120 minutes.
16) The method of any one of embodiments 10-15, wherein the immunogenic HA is quantified by liquid chromatography-electrospray ionization-tandem mass spectrometry (LC-ESI-MS).
17) The method of any preceding embodiment, as dependent on embodiment 1 or 10, wherein the step of separating the immunogenic HA comprises protein precipitation.
18) The method of embodiment 17, wherein the protein precipitation comprises a step of adding an organic solvent.
19) The method of embodiment 18, wherein the organic solvent is a ketone or alcohol.
20) The method of embodiment 19, wherein the organic solvent is acetone, ethanol or methanol.
21) The method of any preceding embodiment, as dependent on embodiment 1 or 10, wherein the method comprises a step of washing the precipitated protein with an alcohol.
22) The method of embodiment 21, wherein the alcohol is ethanol.
23) The method of any preceding embodiment, wherein the sample is selected from the group consisting of: a whole virion influenza vaccine, a split influenza vaccine, a subunit influenza vaccine, and a recombinant influenza vaccine.
24) The method of embodiment 23, wherein the sample comprises an adjuvant.
25) The method of embodiment 24, wherein the adjuvant is an oil-in-water emulsion adjuvant.
26) The method of any preceding embodiment, wherein the sample comprises HA from one, two, three, four or more influenza strains.
27) The method of any preceding embodiment, wherein the sample was taken from a monovalent bulk preparation, a multivalent bulk preparation, monovalent product, or multivalent product.
28) The method of any one of embodiments 1-9 or 16-27, wherein the LC-ESI-MS is Isotope Dilution Mass Spectrometry (IDMS).
29) The method of any preceding embodiment, wherein the labeled reference HA peptide comprises an isotope label.
30) The method of embodiment 29, wherein the isotope label is selected from the list consisting of $^{15}N$ and $^{13}C$.
31) A method for quantifying immunogenic influenza HA in a sample, comprising the steps of: (a) subjecting the sample to biological proteolysis; and, (b) quantifying the amount of immunogenic HA in the sample from (a) by a SRID assay.
32) The method of embodiment 31, wherein step (b) is carried out with the use of an antiserum, such as polyclonal antisera (e.g., sheep antisera) and/or suitable monoclonal antibodies.
33) The method of embodiment 32, wherein the biological proteolysis comprises proteolysis with a protease (e.g. a serine protease, such as trypsin).
34) The method of any one of embodiments 31-33, wherein the biological proteolysis is carried out at 37° C.
35) The method of any one of embodiments 31-34, wherein the sample is selected from the group consisting of: a whole virion influenza vaccine, a split influenza vaccine, a subunit influenza vaccine, and a recombinant influenza vaccine.
36) The method of any preceding embodiment, wherein the sample comprises HA from one, two, three, four or more influenza strains.
37) The method of any preceding embodiment, wherein the sample was taken from a monovalent bulk preparation, a multivalent bulk preparation, monovalent product, or multivalent product.
38) The method of any preceding embodiment, wherein: at least 60% of HA in the sample/vaccine is in an active/immunogenic form; and/or, less than 20% of HA in the sample/vaccine is in an inactive form; and/or, the ratio of active:inactive HA in the sample is at least 4:1.
39) A method for manufacturing an influenza vaccine, the method comprising steps of: providing a sample from a bulk preparation comprising an influenza HA; quantifying the amount of immunogenic HA according to the method of any preceding embodiment; and, packaging unit dosage forms from the bulk preparation according to the amount of immunogenic HA in the sample.
40) A method for preparing an influenza vaccine, comprising the steps of: quantifying the amount of HA in a bulk vaccine by the method of any one of embodiments 1 to 38; and preparing a vaccine from the bulk.
41) The method of embodiment 39 or 40, further comprising a step of filtering so as to provide a sterile preparation.
42) The method of any one of embodiments 39-41, further comprising a step of combining with an adjuvant.
43) The method of any one of embodiments 39-42, wherein the unit dosage are in the form of a liquid, a lyophilized solid, a lyophilized powder, or a nasal aerosol.
44) The method of any one of embodiments 39-43, further comprising a step of repeating the method of embodiment 1 following step (c).
45) The method of any one of embodiments 39-44, wherein the bulk is monovalent or multivalent.

EXAMPLES

This invention is further illustrated by the following examples, which should not be construed as limiting.

Example 1

Pre-treatment by Biological Trypsinization

Influenza viral surface HA primarily exists as a trimer in the pre-fusion state, which is the most immunologically relevant state. HA can undergo an irreversible transition to post-fusion state under various stress conditions. Post-fusion HA does not elicit a strong neutralizing immune response.

The sensitivity of pre-fusion HA and post-fusion HA to trypsin digestion was compared by adding freshly prepared trypsin (enzyme:substrate ratio at 1:20) to samples and incubating at 37° C. for 2 hours.

As shown by SDS-PAGE under reducing conditions (FIG. 1A), the control pre-fusion HA (HA1 and HA2) is very resistant to trypsin digestion, even at high protease concentration (HA:Trypsin=5:1). In contrast, low pH induced post-fusion HA1, which underwent conformation changes, became very sensitive to trypsin. Post-fusion HA2, however, still retained its protease resistance.

Samples were also analysed by reverse phase high performance liquid chromatography (RP-HPLC). For RP-HPLC, DTT-reduced samples were resolved by a Waters Alliance HPLC with UV detection using a Pros R1/10 column (Applied Biosystems) and a gradient of 30-35% ACN (0.1% TFA).

RP-HPLC clearly showed that the HA1 peaks remained unchanged in control conditions (pre-fusion control, pH 4.0 treatment only, and trypsin treatment only). However, the HA1 peak significantly diminished in the low pH and trypsin double-treated samples.

A potency assay was developed by combining the pre-treatment step (dubbed biological trypsinization) with quantitative mass spectrometry. Optimization of biological trypsinization focused on achieving the maximum level of digestion of post-fusion HA1 into short peptides in a short period of time, while not affecting pre-fusion HA1.

Example 2

Protein Precipitation, Analytical Digestion and IDMS

After biological trypsinization, the digested post-fusion HA1 peptides are separated from intact pre fusion HA molecules. A protein precipitation approach was developed and optimized. For protein precipitation, 10 mM Nα-Tosyl-L-lysine chloromethyl ketone hydrochloride (TLCK) freshly made in 1 mM HCl was added to samples that had undergone biological trypsinization, to a final concentration of 100 µM and incubated at room temperature for 10 min. Four fold volume of cold acetone was added to the solution and incubated at −20° C. for 2 hours. The mixture was subsequently centrifuged at ~21 k RCF to pellet the precipitant. Supernatant was carefully removed. The precipitant was then washed three times in 1 mL of cold ethanol. Caution was taken not to disturb the precipitant. Finally, the precipitant was air-dried for 10 min.

The advantage of this approach includes the fact that sample preparation is in the same tube, which minimized sample loss. This also provided convenient re-suspension of recovered protein pellets in desired volume of compatible buffer for downstream sample preparation. This approach led to the introduction of fewer artefacts.

Figure 6:
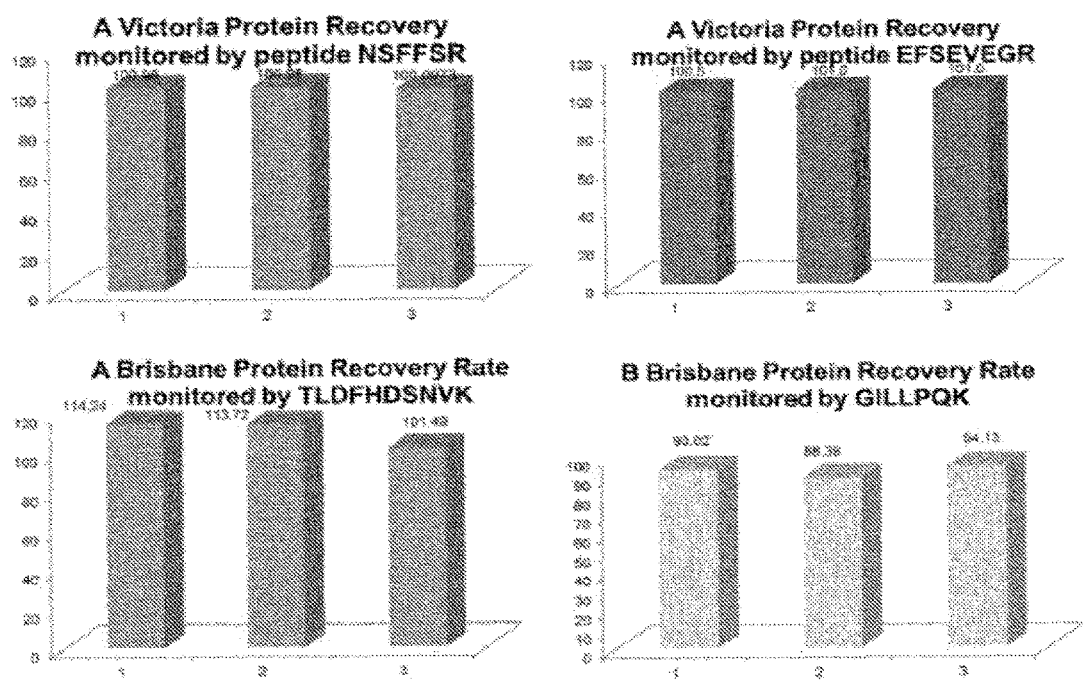

With this optimized protocol, nearly 100% intact HA molecules were recovered consistently, in most cases with acetone protein precipitation (see FIG. 6), and removed 97-100% of digested peptides with ethanol washing (see FIG. 7).

Following separation, the recovered protein pellets were re-suspended in 6 M guanidine HCl (in 50 mM Tris, pH 8.0) and heated at 70° C. for 5 min for complete re-solubilization. Before digestion, the guanidine buffer was diluted to 0.6 M by adding 100 mM Tris (pH 8.0). Trypsin/Lys-C mixture was then added (enzyme:substrate ratio of 1:5) and incubated at 37° C., to begin the analytical digestion that generates peptides for direct isotope dilution mass spectrometry (IDMS) analysis. Time course study showed that under the selected conditions, most if not all targeted surrogate peptides signals reached plateau after 4 h. The digestion was quenched by adding 20% TFA to a final concentration of 2%.

A cocktail of labelled surrogate peptides was added to the reaction mixture and serial concentrations of standard surrogate peptides were made in digestion buffer to generate standard calibration curves. Liquid chromatography standard reaction monitoring (LC-SRM) was performed using a Thermo TSQ Endura Triple Quadrupole MS equipped with an Electrospray Ionization Source (ESI) and coupled to a Dionex Ultimate 3000 UHPLC. Chromatography was performed using a Waters Acquity BEH C18 (2.1×50 mm, 1.7 µm particles) at flow rate of 0.25 mL/min at 50° C. column temperature. SRM was performed essentially as described in the literature (ref. 14) with 3 transitions monitored for each peptide. Data were analyzed by Skyline software and Thermo Qual Browser.

Since the HA2 subunit was resistant to proteolysis, surrogate peptides were selected only from the HA1 sequence. Depending on the purpose of the assay, selection criteria for surrogate peptides vary. If the goal was to quantify total HAs, then conserved sequences across strains were selected as surrogate peptides. If the goal was to quantify specific strains in multivalent samples, then sequences unique to each strain of interest were selected as surrogate peptides. Generally, at least 2 surrogate peptides were used for each strain.

Figure 2:
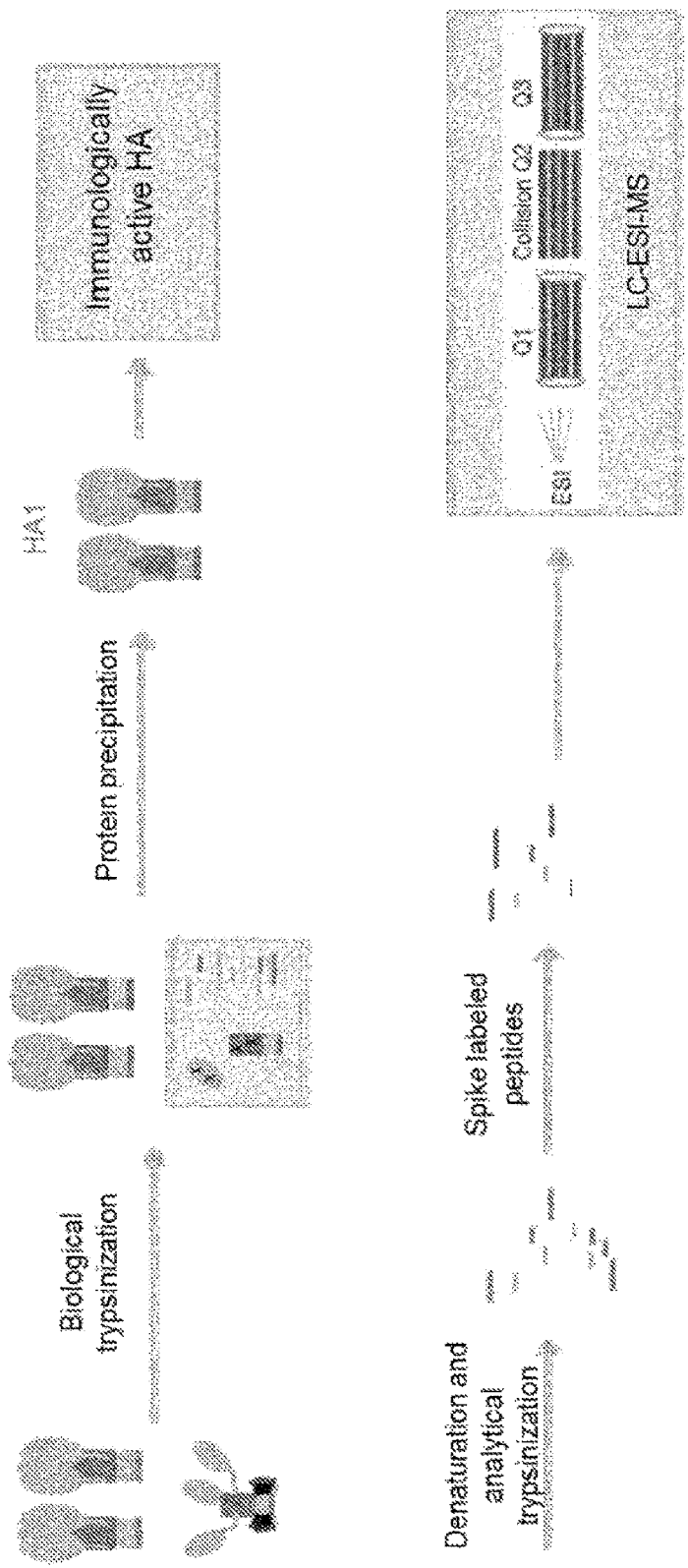

A summary flow chart of the whole assay is shown in FIG. 2.

Example 3

Assay Compatibility with Adjuvant

Adjuvants have been widely used in vaccines to boost their efficacy. The oil-in-water emulsion adjuvant MF59 was one of only a couple of adjuvants that have been used in influenza vaccines and had been linked to significantly improved protection in immuno-deficient/compromised population (ref. 101). Thus, it will be advantageous if the alternative potency assay is compatible with adjuvants.

Three different HA monobulks were tested in the presence or absence of an MF59 adjuvant using the assay of the invention to determine whether the assay is compatible with adjuvants. The data show that the presence of MF59 did not interfere with the assay (Table 1).

TABLE 1

Potency assay is compatible with MF59.

| Strain Name | Condition | Protein concentration (µg/mL) | Ratio (MF59/Control) |
|---|---|---|---|
| A Brisbane | With MF59 (n = 3) | 11.48 | 95% |
|  | No MF59 (n = 3) | 12.12 |  |
| B Brisbane | With MF59 (n = 3) | 20.38 | 103% |
|  | No MF59 (n = 3) | 19.79 |  |
| A Victoria | With MF59 (n = 3) | 11.13 | 109% |
|  | No MF59 (n = 3) | 10.16 |  |

Example 4

Quantification of HA in Stressed Multivalent Vaccines

The assay was used to test influenza vaccines stressed under low pH, high pH, and elevated temperature to confirm the stability-indicating feature of the assay. Due to the nature of LC-SRM based quantification, which is highly selective and capable of quantitating thousands of SRM transitions during a single run, the current assay has the intrinsic advantages in simultaneously quantitating different strains in a multivalent vaccine as long as unique surrogate peptides are used for each strain. Thus, a quadrivalent vaccine was used in this assay, which included 30 µg (based on SRID values) each of A/Victoria/210/2009, A/Brisbane/59/2007, B/Brisbane/60/2008, and B/Wisconsin/1/2010. Stressed or non-stressed control samples, each with or without pretreatment (biological trypsinization) were tested in parallel by RP-HPLC, SRID, and the current assay.

Low pH Stress

Low pH triggers conformational transition of HA from pre-fusion to post-fusion (ref. 9). Low pH stressing was initiated by adding 0.5 M sodium acetate (pH 4.0) to a QIV sample (~120 μg/mL HA, final pH ~4.1), and the sample was further incubated at room temperature for 1 hour. Stressing was quenched by adding 1 M Tris (pH 8.5) to neutralize the pH to ~7.1. The low pH negative' control samples were treated the same way except that H$_2$O was used instead of sodium acetate.

For the low pH stressing experiment, RP-HPLC showed that the HA1 peaks corresponding to all 4 strains almost disappeared in pH 4.0 and biological trypsinization double treated samples (low pH+/trypsin+), which indicated that biological trypsinization removed post-fusion HAs. For 'low pH−/trypsin+' sample, the HA1 peaks were largely intact, indicating that biological trypsinization did not affect the pre-fusion HA.

For the samples without biological trypsinization, the HA1 peaks were also unchanged regardless of the presence or absence of low pH stressing, which was expected since RP-HPLC could not differentiate between pre-fusion or post-fusion HAs (see FIG. 3A).

Quantification results with the current assay showed dramatic drops for all 4 strains in the double treated samples, while results for 'low pH+/trypsin−' samples remained unchanged, which indicated the necessity of the biological trypsinization step.

Only very slight decrease for selected strains was detected for 'low pH−/trypsin+' sample, presumably due to low levels of pre-existing post-fusion HAs in the control sample (FIG. 3B).

SRID testing of the same set of samples showed dramatic drops in low pH treated samples regardless of presence/absence of biological trypsinization (FIG. 3B), confirming low pH induced post-fusion conversion.

This dataset indicates that HA proteins from different strains were all extremely sensitive to low pH stressing. Furthermore, when employing a biological trypsinization step, the assay of the present invention can readily differentiate immunologically active pre-fusion HA from immunologically inactive post-fusion HA.

High pH and Heat Stress

The same experimental scheme was carried under high pH stress (deamidation) and heat stress (56° C.) conditions.

High pH stressing was initiated by adding 0.2 M of N-cyclonhexyl-3-aminopropanesulfonic acid (CAPS) buffer to a QIV sample (final pH~11), and incubated at 37° C. for 2 hours, after which sodium acetate (pH 4.0) was added to neutralize the pH. 'High pH negative' control samples were included using H$_2$O instead of CAPS buffer. For heat stress, samples were treated at 56° C. for 6 hours. For 'trypsin negative' samples, blank buffer was added instead of trypsin.

As for low pH stress, excellent correlation between the assay of the present invention and RP-HPLC/SRID results confirmed that the biological trypsinization step provided the stability-indicating feature to the proposed alternative potency assay (FIGS. 4-5).

Under these conditions, the data suggested that HA proteins were less sensitive to high pH and heat stress, and the sensitivity seemed to be strain-specific. For example, A/Victoria/210/2009 (H3N2) was highly sensitive to elevated temperature, while A/Brisbane/59/2007 (H1N1) potency was not significantly affected by 6 hours heating at 56° C.

In addition, the data set confirmed the capability of the current assay to quantify specific strains in multivalent vaccines without cross-interference.

Example 5

Measuring Mixed Monobulks

B/Brisbane, A/Brisbane and A/Vitoria monobulk samples were tested using the assay of the present invention and compared with a mixed monobulk sample of the same strains mixed in a 1:1:1 ratio.

The quantification of HA in the mixed monobulk sample was the same as in the single monobulk sample (see Table 2). This indicates that the assay is able to quantify specific strains in multivalent samples.

TABLE 2

Comparison of signature peptides in single or mixed strain digests.

| Strain | Peptide | Ratio (native/ standard) in Single | Ratio (native/ standard) in Mixture | Ratio Comparison (Single/ Mixture) |
|---|---|---|---|---|
| A/Brisbane | YAFALSR | 9.41 | 8.33 | 1.13 |
|  | TLDFHDSNVK | 0.34 | 0.30 | 1.13 |
| B/Brisbane | GILLPQK | 0.38 | 0.38 | 1.00 |
|  | NLNSLSELEVK | 0.56 | 0.58 | 0.97 |
| A/Victoria | NSFFSR | 0.77 | 0.79 | 0.97 |

Example 6

Trypsin Pre-treatment Corrects SRID Over-estimation of Immunologically Active HA Caused by Mixed Immunoprecipitin Rings Each monomeric HA subunit, consisting of disulfide-linked HA1 and HA2 fragments, has two domains exposed outside the virus envelope (or cell membrane): a globular "head" composed entirely of HA1 residues, an elongated "stem" composed of residues from HA1 and HA2, and transmembrane and cytoplasmic domains composed of HA2 residues (Wiley and Skehel 1977). HA generally maintains a "metastable," pre-fusion conformation at neutral pH. Once an energy barrier is overcome by low pH, HA refolds irreversibly to a more stable, post-fusion conformation (Ruigrok, Aitken et al. 1988, Bullough, Hughson et al. 1994, Skehel and Wiley 2000). Heat can also trigger HA rearrangement (Ruigrok, Martin et al. 1986, Wharton, Skehel et al. 1986). Immunization with HA in the pre-fusion conformation elicits significant immunity against influenza; immunization with HA in the post-fusion conformation fails to elicit binding and neutralizing antibodies in mice (Quan, Li et al. 2011).

The protective efficacy and immunogenicity of inactivated influenza vaccines ("IIVs"), in principle, can be assessed by immunizing experimental animals, but such in vivo potency testing is time-consuming and imprecise. Instead, more practical in vitro potency assays have been developed to determine the quantity of HA in IIVs that is immunologically active (able to elicit neutralizing or hemagglutination inhibiting [HI] antibody responses). Single radial immunodiffusion (SRID) as a surrogate in vitro potency test for influenza vaccine antigen content was developed and validated in the 1970s (Schild, Wood et al. 1975, Wood, Schild et al. 1977, Williams 1993). This modified Ouchterlony test quantifies HA based on the diameter of the immunoprecipitin ring that forms when vaccine antigen (or an antigen standard homologous to the precise strain in the vaccine) diffuses radially from a circular well into an agarose gel that has been cast with a homogeneous concentration of a strain-specific sheep antiserum. The immunopreciptin ring is detected by Coomassie blue staining, after free antigen and antibody are removed by blotting with filter paper. Although HA in IIVs forms rosettes and other complexes, Zwittergent is added to the antigen to disperse HA to homogenous trimers so that the ring size is more directly proportional to the HA concentration (Williams 1993).

The strain-specific antisera in the agarose SRID gels are generated by immunizing sheep multiple times with HA cleaved from whole virus by bromelain (Brand and Skehel 1972). SRID is believed to produce a readable immunoprecipitin ring only with a native form of HA, because the antisera are raised against HA cleaved from virions and presumed to be native (Minor 2015). Correlation has been shown between SRID-measured vaccine potency and vaccine immunogenicity in clinical trials, although the correlation is relatively weak (Ennis, Mayner et al. 1977, La Montagne, Noble et al. 1983, Rowlen 2015). SRID has been accepted by regulatory agencies and used for influenza vaccine manufacture for IIV formulation, release, and stability testing for four decades.

In contrast, biophysical assays for HA quantity, such as reversed-phase high pressure liquid chromatography (RP-HPLC), isotope dilution mass spectrometry (IDMS), and SDS-PAGE, denature HA before quantification, so that they do not distinguish different conformational states of HA. The Examples above have shown that trypsin digestion can be used as a pre-selection step to confer conformational specificity on an alternative, biophysical influenza potency assays that does not require strain-specific antibodies and would not otherwise be conformationally sensitive (Wen, Han et al. 2015). The basis for this pre-treatment is the trypsin resistance of native, pre-fusion HA and the trypsin sensitivity of post-fusion HA and of HA subjected to other stresses (Skehel, Bayley et al. 1982, Ruigrok, Martin et al. 1986). Trypsin selectively degrades immunologically inactive HA.

This Example further demonstrates that, with conformationally homogenous HA preparations, SRID does indeed detect and quantify non-stressed, presumably pre-fusion HA that is immunogenic in mice and does not detect low-pH-stressed, presumably post-fusion HA that is not immunogenic in mice. The post-fusion HA is selectively removed from the SRID gel during the blotting step. The sheep antiserum used in SRID detects both forms of HA equivalently when used in an ELISA format, suggesting that the conformational selectivity of SRID is due to the SRID format, not due to any conformational selectivity of the antiserum. When low-pH stressed HA is mixed with non-stressed HA, SRID does not distinguish between the pre-fusion and post-fusion forms, detecting both conformers efficiently in mixed immunoprecipitin rings and over-estimating the content of immunologically active HA in the sample. Just as trypsin pre-treatment allows RP-HPLC to specifically quantify immunologically active HA, trypsin digestion also improves the accuracy of SRID, allowing the assay to quantify immunologically active HA when mixed with immunologically inactive HA.

Results

Immunogenicity of HA Exposed to Reduced pH in Mice

To assess the immunogenicity of HA in pre-fusion and post-fusion conformation, mice were immunized twice with 0.1 µg of egg-produced A/Texas/50/2012 (H3N2) HA incubated in pH 4.0 buffer and then returned to pH 7.2 (assumed to be in the post-fusion conformation) or maintained at a constant pH 7.2 (assumed to be in the pre-fusion conformation). HI was performed to evaluate the titers of antibodies present in mouse immune sera that could block hemagglutination of turkey red blood cells by A/Texas/50/2012 (H3N2) virus. HA maintained at pH 7.2 elicited a GMT HI titer of $3\times10^2$, and HA transiently exposed to pH 4.0 elicited a GMT HI titer of <10 (FIG. 8A). Microneutralization assays were also used to quantify the neutralizing antibody titers blocking infection of Madin-Darby Canine Kidney (MDCK) cells with A/Texas/50/2012 (H3N2) virus, showing similar results (FIG. 8B). HA stressed by low pH did not elicit a detectable neutralizing response, and HA maintained at neutral pH elicited a significant neutralizing antibody titer. Thus, HA in the pre-fusion conformation was significantly more immunogenic in mice than HA in the post-fusion conformation, consistent with previous findings (Quan, Li et al. 2011). The HA samples were also digested with trypsin under native conditions and used to immunize mice. Both HI and microneutralization assays showed that the HI and neutralizing antibody responses to HA were not affected by trypsin digestion (FIG. 8).

Characterization of HA Exposed to Reduced pH by SDS-PAGE, RP-HPLC, ELISA and SRID The same A/Texas/50/2012 (H3N2) HA samples were further characterized by SDS-PAGE under both non-reducing and reducing conditions. SDS-PAGE band intensities for HA maintained at pH 7.2 and transiently exposed to pH 4.0 were comparable (FIG. 9A). Consistent with our previous findings (Wen, Han et al. 2015). After trypsin treatment under native conditions, SDS-PAGE bands for HA (with non-reduced samples) and HA1 (with reduced samples) stressed by low pH disappeared while those for HA maintained at pH 7.2 were unchanged. Similarly, RP-HPLC HA1 peaks from un-digested HA with and without low-pH treatment were almost identical (FIG. 9B). However, after trypsin digestion, only the HA1 peaks for HA treated by low pH disappeared. ELISA with SRID reference antiserum against A/Texas/50/2012 (H3N2) HA was performed on these HA samples. Un-digested HA that was un-stressed or stressed with low pH were recognized similarly by the SRID antiserum in the ELISA format (FIG. 8C). Trypsinization slightly decreased the ELISA signal (<15% decrease) for HA maintained at pH 7.2, but significantly decreased the ELISA signal (>50% decrease) for low-pH stressed HA. These results suggested that although SDS-PAGE, RP-HPLC and ELISA showed similar results for low-pH stressed and non-stressed HA, when coupled with trypsinization, these assays were able to distinguish HA maintained at neutral pH from HA stressed by low pH, yielding results correlating with those from the immunogenicity study (FIG. 9E).

SRID was also performed on these HA samples. As expected, distinct SRID rings were detected for HA maintained at neutral pH with and without trypsinization, and no SRID rings were detected for HA exposed to low pH regardless of whether the samples were trypsin digested (FIG. 9D). Therefore, SRID self-sufficiently distinguished non-stressed HA immunogenic in mice from low-pH stressed HA significant less immunogenic (FIG. 8), so were SDS-PAGE, RP-HPLC and ELISA once combined with the trypsinization step (e.g., biological proteolysis) (FIG. 9E).

SRID Quantification of Non-stressed HA Spiked with Low-pH Stressed HA

Egg-produced A/Perth/16/2009 (H3N2) HA was evaluated by SRID, and the same results were obtained as for A/Texas/50/2102 (H3N2): non-stressed HA was detected with positive SRID rings, and low-pH stressed HA produced no rings (FIG. 10A). Surprisingly, when non-stressed HA was spiked with low-pH stressed HA, the SRID rings reduced in intensity but expanded in a dose-response fashion with the increasing amount of added low-pH treated HA (FIG. 10A). Quantification of ring sizes confirmed that the detected HA quantity increased 25% to 70% with 0.5- to 2-fold amounts of low-pH stressed HA added to non-stressed HA (FIG. 10B). This set of samples was also quantified with RP-HPLC following trypsinization, and the relative HA quantities were maintained at 100% compared to non-stressed HA alone (FIG. 10B). These results showed that, when stressed and non-stressed HA were mixed, SRID detected both forms of HA, losing its specificity for immunologically active HA.

We next investigated whether this SRID over-estimation of immunologically active HA in mixtures of stressed and non-stressed HA was reproducible with additional HA samples of different influenza strains. Egg-produced B/Brisbane/60/2008 HA was evaluated by SRID, and produced positive SRID rings for non-stressed HA and negative rings for low-pH stressed HA, when non-stressed and stressed HA preparations were analyzed separately (FIG. 11A). However, when non-stressed B/Brisbane/60/2008 HA was mixed with an equal amount of low-pH stressed HA, the SRID rings were enlarged, leading to a relative measured HA quantity of 150% compared to non-stressed HA alone (FIG. 11B). Trypsin treatment before SRID did not change the relative HA quantity for non-stressed HA nor stressed HA alone, but decreased the measured HA content for the mixture of non-stressed and stressed HA to the amount of non-stressed HA alone and made the immunoprecipitin rings more distinct (FIG. 11A). As expected, RP-HPLC quantified the total HA content in the mixture at 200% of the non-stressed quantity alone; with trypsin pre-treatment, quantification of the mixture by RP-HPLC also decreased to the amount of non-stressed HA only.

Additional HA samples, egg-produced A/California/07/2009 (H1N1), A/Texas/50/2012 (H3N2), B/Massachusetts/02/2012 were also quantified with SRID and RP-HPLC (FIGS. 11C, 11D and 11E). In each case, the addition of the equal amount of low-pH stressed HA into non-stressed HA led to 30 to 50% increases of HA quantities measured by SRID. Trypsin digestion as pre-step brought the relative SRID quantification back to 100% of the non-stressed sample. RP-HPLC alone quantified total HA in the mixture with relative quantity as 200% of the non-stressed sample. Trypsinization also decreased the quantity by RP-HPLC to 100%. These results confirmed that, when low-pH stressed HA is mixed with non-stressed HA, SRID quantified the stressed HA at 20-50% of non-stressed HA instead of 0%. In contrast, in vivo potency testing indicated that the low-pH stressed HA was immunologically inactive (FIG. 8). Trypsin treatment not only enabled RP-HPLC to selective quantify non-stressed HA but also corrected the SRID over-estimation of immunologically active HA.

Mechanism of SRID Quantification of HA

To understand the mechanism of SRID better, we labeled HA and tracked it as it diffused into an SRID gel. Egg-produced A/Texas/50/2012 (H3N2) HA was transiently exposed to low pH or maintained at pH 7.2, then conjugated with IRDye 800CW maleimide through one free cysteine located on each HA2. SDS-PAGE with infrared fluorescent scanning confirmed the HA2-specific labelling and equal labelling efficiency on non-stressed and stressed HA (data not shown). IRDye-labeled HA and non-labeled HA were evaluated by SRID assay. HA samples were loaded in the wells of an SRID gel and allowed to diffuse into the gel for 16 hours at room temperature. IRDye-labeled HA, either non-stressed or low-pH stressed, diffused in the gel to a similar distance from the wells (FIG. 12A). Instead of filter paper, a nitrocellulose membrane was used to blot away free antigen and antibody. The fluorescent signal on the membrane for low-pH stressed HA was stronger than that for non-stressed HA. The western blotting with anti-H3 antibody to the blotting membrane for the non-labeled HA confirmed that more low-pH stressed HA than non-stressed HA was removed onto the blotting membrane. The fluorescent signal of post-blotting SRID gel showed distinct immunoprecipitation rings for non-stressed HA samples and weak, smeared signals for low-pH stressed HA. Coomassie blue staining of the same SRID gel confirmed the expected SRID ring for non-stressed HA and no ring for low-pH stressed HA. These results suggested that the negative SRID signal for low-pH stressed HA was caused by its removal by blotting during the SRID assay. Coomassie blue staining of SRID gels for labeled and non-labeled HA showed identical SRID ring profiles, confirming that labeling of HA has no detectable impact on HA quantification by SRID.

We next labeled non-stressed HA with IRDye800SW, which has a green fluorescent signal, and low-pH stressed HA with IRDye680CT, which has a red fluorescent signal, and analyzed the samples by SRID (FIG. 12B). The green signal showed an SRID ring formed by immune complexes containing non-stressed HA, but no red ring corresponding to immune complexes containing low-pH stressed HA was visible. Coomassie blue staining showed equivalent results. For a mixed sample containing non-stressed and stressed HA with ratio of one-to-one, non-stressed HA formed a green ring larger than the one observed in the absence of low-pH stressed HA. Low-pH stressed HA in the mixture also formed a well-defined large red ring. The overlayed image showed that the rings for non-stressed HA and low-stressed HA overlapped, suggesting that non-stressed and stressed HA associated together directly or indirectly in mixed immunoprecipitin rings. The larger ring was also detected by Coomassie blue staining indicating that more total HA diffused further away from the well, reflecting the combined amount of stressed and non-stressed HA. When the mixed sample was digested by trypsin, the green ring formed by non-stressed HA returned to its original size, and the red ring formed by stressed HA disappeared. The Coomassie-stained ring also returned to the size of that formed by non-stressed HA alone. These results suggested that trypsin digested the stressed HA capable for forming mixed immunoprecipitin rings with non-stressed HA.

Discussion

The integrity of HA can be compromised by a number of stress conditions that commonly affect biologic products during vaccine production and storage. In addition, because HA is primed to rearrange at modestly low pH (to carry out its membrane fusion function during viral entry into cells), HA in influenza vaccines is particularly sensitive to low pH exposure. Although the immunogenicity of HA subjected to the full range of stresses has not been completely explored, it is shown in this study (FIG. 8) and other studies (Quan, Li et al. 2011) that HA in the pre-fusion state elicits more potently neutralizing antibodies in mice than HA triggered to rearrange into the post-fusion state by low pH. Thus, HA-based vaccine potency assays should be sensitive to HA conformation.

SRID, the "gold standard" surrogate assay for IIV potency (Williams 1993), relies on sheep antisera for potency determination (Wood, Schild et al. 1977). Sheep antisera are raised with HA extracted from purified whole virus, which may or may not be entirely in a native, pre-fusion conformation. In our study, a sheep polyclonal antiserum used for SRID bound to HA in both pre-fusion and in post-fusion conformation equivalently well in an ELISA format (FIG. 9C), suggesting that a major portion of the antibodies was not specific to native, pre-fusion HA. Therefore, the selective detection of pre-fusion HA, but not post-fusion HA by SRID must have been determined by the SRID format, not by the specificity of sheep antiserum alone.

The underlining premise of SRID is that the assay quantifies HA based solely on the size (diameter) of an immunoprecipitin ring, such that the larger the ring, the higher the HA concentration assigned (Williams 1993). Neither the intensity nor the sharpness of ring is considered in assay interpretation. HA in IIV forms rosettes and other aggregates through HA-HA, HA-other viral protein, and HA-cellular membrane interactions (Tay, Agius et al. 2015). The pre-treatment of vaccine antigen with Zwittergent for SRID analysis disperses HA to smaller oligomers but not to entirely homogeneous HA trimers (data not shown). Therefore, in the SRID gel, heterogeneous forms of HA diffuse to various distances from the well, so that the estimated HA quantity does not correlate simply to HA concentration alone.

With pure preparations of low-pH stressed or non-stressed HA, SRID did show specificity for the immunologically active, non-stressed form. Further investigation showed that the post-fusion HA diffused into the SRID gel like pre-fusion HA but was selectively removed from the gel by the blotting step before detection by Coomassie staining. The reason for the selective blotting of post-fusion HA is not entirely clear. It is possible that the sheep antiserum cross-links a pure preparation of post-fusion HA less extensively than a pure preparation of pre-fusion HA (despite similar detection of the forms in an ELISA format).

In a vaccine preparation, a lesser or greater proportion of denatured, damaged, or post-fusion HA is expected to be present, together with native, intact, pre-fusion HA. In our experiment, SRID detected low-pH stressed HA when it was mixed with native HA, even though the assay did not detect low-pH stressed HA alone. This observation was reproduced with HA from a number of strains. Differential labeling of non-stressed and low pH-stressed HA with alternative fluorescent signals showed that low-pH stressed, post-fusion HA formed mixed immunoprecipitin rings with native, pre-fusion HA, suggesting these two species of HA associated together directly or indirectly. Sheep antisera bind to both forms of HA equally in ELISA, they apparently can also cross-link with both HA conformers and form the three-component complexes detectable on SRID. The mixed rings were less distinct after Coomassie staining than pure pre-fusion rings, perhaps reflecting compromised cross-linking of the HA mixture by the sheep antiserum. Nevertheless, with a higher HA concentration in the complex, larger ring sizes than those formed by native HA and antiserum alone were produced, resulting in an over-estimation of the immunologically active HA content.

Under native conditions, trypsin selectively digests HA affected by low-pH, raised temperature and deamination (Wen, Han et al. 2015). By removing immunologically inactive HA, trypsin digestion can be used as a pre-treatment before efficient and accurate biophysical HA quantification techniques that denature HA, adding conformational sensitivity to the assays. Here, we showed that trypsin pre-treatment returned enlarged, mixed SRID rings to the size corresponding to the concentration of native HA alone. The fluorescent signals for postfusion HA were not detectable in SRID rings formed by mixtures of trypsin digested low pH-stressed and non-stressed HA, suggesting that the digestion removed post-fusion HA capable of forming detectable three-component immunoprecipitin rings.

SRID is formally approved by the WHO and national regulatory bodies for the quantification of influenza vaccine potency and is extensively used by influenza vaccine manufacturers as the "gold standard" for HA quantification. Indeed, a need to match SRID in HA quantification is a barrier to the introduction of potentially more accurate, precise, and efficient influenza vaccine potency assays. We have shown here that SRID systematically overestimates immunologically active HA when it is mixed with post-fusion HA. Just as trypsin pre-treatment can confer conformational selectivity on biophysical HA quantification assays that do not require generation of a sheep antiserum for each strain change, trypsin pre-treatment can also correct the overestimation of immunologically active HA by SRID. This correction could improve vaccine formulation and release by SRID and could also facilitate the introduction of improved potency assays by providing a more "pure gold" standard to match.

Methods

Influenza Reference Reagents

Sheep polyclonal reference antisera and calibrated reference antigens for A/California/07/2009 (H1N1), A/Texas/50/2012 (H3N2), A/Perth/16/2009 (H3N2), B/Massachusetts/02/2012 and B/Brisbane/60/2008 were provided by the US Food and Drug Administration's Center for Biologics Evaluation and Research (FDA CBER, Silver Spring, Md.) and the National Institute for Biological Standards and Control (NIBSC, London, UK).

Influenza Vaccines

A/California/07/2009 (H1N1), A/Texas/50/2012 (H3N2), A/Perth/16/2009 (H3N2), B/Massachusetts/02/2012 and B/Brisbane/60/2008 monobulks (unblended lots of subunit vaccine antigen) were produced by Novartis Vaccines. The egg-produced monobulks were produced from embryonated chicken eggs by the Agrippal® subunit influenza vaccine process from pilot or engineering batches.

Sample Stress by Low-pH

Influenza monobulks were treated with 50 mM citrate at pH 4.0 at room temperature for 30 minutes. 10% (volume/volume) of 1 M Tris at pH 8.5 was added to neutralize the pH to 7.2. Samples were stored at 4° C. until analyzed.

Trypsin Digestion

Samples were incubated with trypsin (50 U/100 µg HA, Sigma, St. Louis, Mo.) in PBS at 37° C. for 120 min. Trypsin digestion was stopped by the addition of 0.1 mM N-α-tosyl-L-lysinyl-chloromethylketone (TLCK; Sigma). Samples were stored at 4° C. until analyzed.

SDS-PAGE, RP-HPLC, ELISA and SRID

SDS-PAGE, RP-HPLC and SRID have been described in (Wen, Han et al. 2015). For direct ELISA, plates were coated overnight at room temperature with 1 µg/ml A/Texas/50/2012 (H3N2) HA in PBS, washed with 0.05% Tween-20 in PBS (PBST) four times and blocked with 1% BSA in PBS (PBSB) for 60 minutes. Serial dilutions of sheep sera in PBSB were then incubated on the plates for 90 minutes. Plates were washed with PBST four times and captured IgG was detected with horse radish peroxidase-conjugated goat anti-sheep IgG (Invitrogen) for 60 minutes, followed by washing with PBST four times and incubation with tetramethylberzidinesubstrate for 30 minutes. The plates were read by Infinite M200 NanoQuant (Tecan).

Immunogenicity Studies

Eight-to-ten-week old female BALB/c mice (Charles River Labs, Wilmington, Mass., USA) were immunized (10 mice/group) by bilateral 50 µl intramuscular injections in the rear quadriceps on days 0 and 21 with 0.1 µg of HA. Serum samples were obtained by retro-orbital sinus bleeds on day 20 and from bleed-outs of euthanized animals on day 42. All studies were approved by the Novartis Institutes for Biomedical Research Animal Care and Use Committee.

Serological Analysis

Serum samples were tested for neutralizing antibodies by HI and influenza micro-neutralization assays.

For HI, serum samples heat-inactivated at 56° C. for 30 min with receptor destroying enzyme (RDE), were serially diluted, and then incubated with A/Texas/50/2012 (H3N2) virus in 96-well plates at 2-8° C. for 60 min. Turkey red blood cells (Lampire Biological labs) were added and mixed in each well, and the mixtures were incubated at 2-8° C. for 90 min.

For micro-neutralization, inactivated serum samples were serially diluted, and then incubated with A/Texas/50/2012 (H3N2) virus at 37° C. for 2 hours. These serum and virus mixtures were added to MDCK cells prepared in 96-well plates and incubated overnight at 37° C. The infected cells were fixed with ice cold 1:1 acetone:methanol solution, blocked with PBSB, and incubated with primary anti-influenza A antibody (Millipore). After incubation with secondary goat anti-mouse IgG conjugated with Alexa Fluor 488 (Invitrogen), the fluorescent cells were counted using an Immunospot S5 UV Analyzer (CTL).

IRDye-labelling of HA

HA in PBS was incubated with IRDye 800CW maleimide or IRDye 680CT (LI-COR) reconstituted in water at room temperature for 2 hrs. Free IRDye was removed by Zeba desalt spin columns (Pierce), following the protocols provided by vendors. IRDye was detected by an Odyssey CLx imager (Licor).

Example 7

Correlation Between RP-HPLC and SRID Potency Assay Results and Immunogenicity Studies Using Influenza Antigen Samples Exposed to a Panel of Stress Conditions Influenza vaccine potency assays of the present invention can provide results having excellent correlation with SRID and immunogenicity studies (hemagglutinin inhibition (HI) assay and microneutralization (MN) titers), using antigen from various A and B virus subtypes exposed to various stress conditions. For example, see Examples 4 and 6 and FIGS. 3-5 and 8-9.

The inventors have carried out further studies using antigens from H3N2 and H1N1 subtype influenza A virus strains. Antigen monobulks were split into identical groups, each of which was then exposed to a different stress condition, including low pH (pH 4.0 for 30 min), freeze/thaw (5× in Tris buffer), deamidation (pH 11.0 at 37° C. for 24 hrs), and vortex stress (vortex at room temperature for 30 min), or to no stress (control). HA quantity was measured in a sample from each group using RP-HPLC and SRID, without or with pre-trypsinization. The inventors found that the relative HA quantity (e.g. relative to SRID results for control group, without pre-trypsinization) as measured by RP-HPLC without pre-trypsinization did not correlate well with SRID results (with or without pre-trypsinization), for all stress conditions tested. In contrast, relative HA quantity as measured by RP-HPLC with pre-trysinization correlated well with SRID results, especially for SRID carried out with pre-trypsinization. For example, low pH (significantly) and deamidation (slightly) decreased HA quantity as measured by SRID (with or without trypsinization), and by RP-HPLC with pre-trypsinization. Freeze/thaw and vortex stress did not significantly decrease HA quantity as measured by SRID (with or without trypsinization), or by RP-HPLC with pre-trypsinization.

Immunogenicity of the same stressed and control H3N2 antigen sample groups was further tested using HI and MN assays. Antisera for each group were generated by administering antigen from each group (0.1 µg HA dose) to 8 BALB/c female mice per group at days 0 and 21, using the day 42 bleed (three weeks post second immunization). Antisera were then used in HI and MN assays. Preliminary results confirmed that immunogenicity as measured by HI and MN correlated with relative HA quantities as determined by RP-HPLC and SRID, with pre-trypsinization for at least the low pH, freeze/thaw and vortex stress groups.

REFERENCES

1) Williams (1993) Vet Microbiol 37:253-262.
2) Fitzgerald & Needy (1986) Dev Biol Stand 64:73-79.
3) WO 2010/136896
4) Kapteyn, et al.; Vaccine 2009; 27:1468-77.
5) Lorbetskie et al.; Vaccine 2011; 29:3377-89.
6) Williamsa et al.; Vaccine 2008; 26:2510-20.
7) Santana et al.; Anal Chem 2014; 86:4088-95.
8) Bodle et al.; Influenza Other Respir Viruses 2013; 7:191-200.
9) Skehel et al.; Proc Natl Acad Sci USA 1982; 79:968-72.
10) Böttcher et al.; J Virol. 2006 October; 80(19): 9896-9898.
11) Kapteyn et al. (2006) Vaccine 24:3137-44
12) WO 2009110873
13) U.S. Pat. No. 6,649,354; U.S. Pat. No. 6,635,452; U.S. Pat. No. 7,132,519
14) Picotti and Aebersold; Nat Methods 2012; 9:555-66.
15) WO 96/37624.
16) WO 02/28422.
17) WO 02/067983.
18) WO 02/074336.
19) WO 01/21151.
20) WO 02/097072.
21) WO 2005/113756.
22) Huckriede et al. (2003) Methods Enzymol 373:74-91.
23) Herlocher et al. (2004) J Infect Dis 190(9):1627-30.
24) Le et al. (2005) Nature 437(7062):1108.
25) WO 2005/113756.
26) WO 97/37000.
27) Brands et al. (1999) Dev Biol Stand 98:93-100.
28) Halperin et al. (2002) Vaccine 20:1240-7.
29) Tree et al. (2001) Vaccine 19:3444-50.
30) Kistner et al. (1998) Vaccine 16:960-8.
31) Kistner et al. (1999) Dev Biol Stand 98:101-110.
32) Bruhl et al. (2000) Vaccine 19:1149-58.
33) Pau et al. (2001) Vaccine 19:2716-21.

36) WO 03/076601.
37) WO 2005/042728.
38) WO 03/043415.
39) WO 01/85938
40) WO 2006/108846
41) Schuind et al.; J Infect Dis. 2015 Feb. 25.
42) EP-A-1260581 (WO 01/64846).
43) WO 2006/071563.
44) WO 2005/113758.
45) WO 2006/027698.
46) Lundblad (2001) Biotechnology and Applied Biochemistry 34:195-197.
47) Guidance for Industry: Bioanalytical Method Validation. U.S. Department of Health and Human Services Food and Drug Administration Center for Drug Evaluation and Research (CDER) Center for Veterinary Medicine (CVM). May 2001.
48) Ji et al. (2002) Biotechniques. 32:1162-7.
49) Briggs (1991) J Parenter Sci Technol. 45:7-12.
50) Lahijani et al. (1998) Hum Gene Ther. 9:1173-80.
51) Lokteff et al. (2001) Biologicals. 29:123-32.
52) EP B 0870508.
53) U.S. Pat. No. 5,948,410.
54) WO 2007/052163.
55) WO 2010/052214.
56) WO 03/023021.
57) WO 03/023025.
58) WO 97/37001.
59) Hoffmann et al. (2002) Vaccine 20:3165-3170.
60) Subbarao et al. (2003) Virology 305:192-200.
61) Liu et al. (2003) Virology 314:580-590.
62) Ozaki et al. (2004) J. Virol. 78:1851-1857.
63) Webby et al. (2004) Lancet 363:1099-1103.
64) WO 00/60050.
65) WO 01/04333.
66) U.S. Pat. No. 6,649,372.
67) WO 2009/000891.
68) Neumann et al. (2005) Proc Natl Acad Sci USA 102:16825-9.
69) WO 2006/067211.
70) WO 01/83794.
71) Hoffmann et al. (2000) Virology 267(2):310-7.
72) WO 2013/087945
73) WO 2014/141125
74) WO 01/22992.
75) Hehme et al. (2004) Virus Res. 103(1-2):163-71.
76) Treanor et al. (1996) J Infect Dis 173:1467-70.
77) Keitel et al. (1996) Clin Diagn Lab Immunol 3:507-10.
78) WO 96/37624.
79) WO 98/46262.
80) Gennaro (2000) Remington: The Science and Practice of Pharmacy. 20th edition, ISBN: 0683306472.
81) Banzhoff (2000) Immunology Letters 71:91-96.
82) Nony et al. (2001) Vaccine 27:3645-51.
83) WO 90/14837.
84) Podda & Del Giudice (2003) Expert Rev Vaccines 2:197-203.
85) Podda (2001) Vaccine 19: 2673-2680.
86) Vaccine Design: The Subunit and Adjuvant Approach (eds. Powell & Newman) Plenum Press 1995 (ISBN 0-306-44867-X).
87) Vaccine Adjuvants: Preparation Methods and Research Protocols (Volume 42 of Methods in Molecular Medicine series). ISBN: 1-59259-083-7. Ed. O'Hagan.
88) WO 2008/043774.
89) US 2007/014805.
90) US 2007/0191314.
91) Fox et al. (2013) Vaccine 31:1633-1640.
92) Allison & Byars (1992) Res Immunol 143:519-25.
93) Hariharan et al. (1995) Cancer Res 55:3486-9.
94) Suli et al. (2004) Vaccine 22(25-26):3464-9.
95) WO 95/11700.
96) U.S. Pat. No. 6,080,725.
97) WO 2005/097181.
98) WO 2006/113373.
99) Han et al. (2005) Impact of Vitamin E on Immune Function and Infectious Diseases in the Aged at Nutrition, Immune functions and Health EuroConference, Paris, 9-10 Jun. 2005.
100) U.S. Pat. No. 6,630,161.
101) Settembre et al.; Hum Vaccin Immunother 2014, 10:600-4.
102) Brand, C. M. and J. J. Skehel (1972). "Crystalline antigen from the influenza virus envelope." Nat New Biol 238(83): 145-147.
103) Bullough, P. A., F. M. Hughson, J. J. Skehel and D. C. Wiley (1994). "Structure of influenza haemagglutinin at the pH of membrane fusion." Nature 371(6492): 37-43.
104) Ennis, F. A., R. E. Mayner, D. W. Barry, J. E. Manischewitz, R. C. Dunlap, M. W. Verbonitz, R. M. Bozeman and G. C. Schild (1977). "Correlation of laboratory studies with clinical responses to A/New Jersey influenza vaccines." J Infect Dis 136 Suppl: S397-406.
105) Knossow, M., M. Gaudier, A. Douglas, B. Barrere, T. Bizebard, C. Barbey, B. Gigant and J. J. Skehel (2002). "Mechanism of neutralization of influenza virus infectivity by antibodies." Virology 302(2): 294-298.
106) La Montagne, J. R., G. R. Noble, G. V. Quinnan, G. T. Curlin, W. C. Blackwelder, J. I. Smith, F. A. Ennis and F. M. Bozeman (1983). "Summary of clinical trials of inactivated influenza vaccine—1978." Rev Infect Dis 5(4): 723-736.
107) Minor, P. D. (2015). "Assaying the Potency of Influenza Vaccines." Vaccines 3: 90-104.
108) Poland, G. A., S. T. Rottinghaus and R. M. Jacobson (2001). "Influenza vaccines: a review and rationale for use in developed and underdeveloped countries." Vaccine 19(17-19): 2216-2220.
109) Quan, F. S., Z. N. Li, M. C. Kim, D. Yang, R. W. Compans, D. A. Steinhauer and S. M. Kang (2011). "Immunogenicity of low-pH treated whole viral influenza vaccine." Virology 417(1): 196-202.
110) Rowlen, K. (2015). "Validation of alternative potency assays for influenza vaccines requires clinical studies." Vaccine.
111) Ruigrok, R. W., A. Aitken, L. J. Calder, S. R. Martin, J. J. Skehel, S. A. Wharton, W. Weis and D. C. Wiley (1988). "Studies on the structure of the influenza virus haemagglutinin at the pH of membrane fusion." J Gen Virol 69 (Pt 11): 2785-2795.
112) Ruigrok, R. W., S. R. Martin, S. A. Wharton, J. J. Skehel, P. M. Bayley and D. C. Wiley (1986). "Conformational changes in the hemagglutinin of influenza virus which accompany heat-induced fusion of virus with liposomes." Virology 155(2): 484-497.
113) Schild, G. C., J. M. Wood and R. W. Newman (1975). "A single-radial-immunodiffusion technique for the assay of influenza haemagglutinin antigen.

Proposals for an assay method for the haemagglutinin content of influenza vaccines." Bull World Health Organ 52(2): 223-231.
114) Skehel, J. J., P. M. Bayley, E. B. Brown, S. R. Martin, M. D. Waterfield, J. M. White, I. A. Wilson and D. C. Wiley (1982). "Changes in the conformation of influenza virus hemagglutinin at the pH optimum of virus-mediated membrane fusion." Proc Natl Acad Sci USA 79(4): 968-972.
115) Skehel, J. J. and D. C. Wiley (2000). "Receptor binding and membrane fusion in virus entry: the influenza hemagglutinin." Annu Rev Biochem 69: 531-569.
116) Tay, T., C. Agius, R. Hamilton, J. Bodle and S. Rockman (2015). "Investigation into alternative testing methodologies for characterization of influenza virus vaccine." Hum Vaccin Immunother 11(7): 1673-1684.
117) Wen, Y., L. Han, G. Palladino, A. Ferrari, Y. Xie, A. Carfi, P. R. Dormitzer and E. C. Settembre (2015). "Conformationally selective biophysical assay for influenza vaccine potency determination." Vaccine 33(41): 5342-5349.
118) Wharton, S. A., J. J. Skehel and D. C. Wiley (1986). "Studies of influenza haemagglutinin-mediated membrane fusion." Virology 149(1): 27-35.
119) Wiley, D. C. and J. J. Skehel (1977). "Crystallization and x-ray diffraction studies on the haemagglutinin glycoprotein from the membrane of influenza virus." J Mol Biol 112(2): 343-347.
120) Wiley, D. C., I. A. Wilson and J. J. Skehel (1981). "Structural identification of the antibody-binding sites of Hong Kong influenza haemagglutinin and their involvement in antigenic variation." Nature 289(5796): 373-378.
121) Williams, M. S. (1993). "Single-radial-immunodiffusion as an in vitro potency assay for human inactivated viral vaccines." Vet Microbiol 37(3-4): 253-262.
122) Wilson, I. A., J. J. Skehel and D. C. Wiley (1981). "Structure of the haemagglutinin membrane glycoprotein of influenza virus at 3 A resolution." Nature 289(5796): 366-373.
123) Wood, J. M., G. C. Schild, R. W. Newman and V. Seagroatt (1977). "An improved single-radial-immunodiffusion technique for the assay of influenza haemagglutinin antigen: application for potency determinations of inactivated whole virus and subunit vaccines." J Biol Stand 5(3): 237-247.
124) Zambon, M. C. (1999). "Epidemiology and pathogenesis of influenza." J Antimicrob Chemother 44 Suppl B: 3-9.
125) Minor, Philip D. (2015). "Assaying the potency of influenza vaccines." Vaccines 3: 90-104.

It will be understood that the invention has been described by way of example only and modifications may be made whilst remaining within the scope and spirit of the invention.

The invention claimed is:

1. A method comprising the steps of:
a) providing a sample comprising immunogenic influenza HA, inactive influenza HA, or a combination thereof;
b) subjecting the sample to biological proteolysis, wherein the inactive influenza HA is digested and the immunogenic influenza HA remains undigested;
c) separating the digested inactive influenza HA from the undigested immunogenic influenza HA in the sample;

d) subjecting the undigested immunogenic influenza HA to analytical proteolysis, so as to provide fragments of digested immunogenic influenza HA;

e) carrying out a liquid chromatography-electrospray ionization-tandem mass spectrometry (LC-ESI-MS) in the presence of at least one labeled reference influenza HA peptide, to quantify the amount of immunogenic influenza HA in the sample;

wherein immunogenic influenza HA is associated with influenza HA in a pre-fusion state and inactive influenza HA is associated with influenza HA in a post-fusion state.

2. A method comprising the steps of:

a) providing a sample comprising immunogenic influenza HA, inactive influenza HA, or a combination thereof;

b) subjecting the sample to biological proteolysis by one or more proteases, wherein the inactive influenza HA is digested and the immunogenic influenza HA remains undigested;

c) subjecting the mixture of undigested immunogenic influenza HA and digested inactive influenza HA to analytical proteolysis using one or more proteases, wherein the analytical proteolysis cannot cleave the immunogenic influenza HA at one or more cleavage site(s) which can be cleaved in the inactive influenza HA during biological proteolysis, so as to provide fragments of digested immunogenic influenza HA that comprise immunogenic influenza HA-derived peptide (s) that is/are distinguishable from the inactive influenza HA-derived peptides; and, f) carrying out liquid chromatography-electrospray ionization-tandem mass spectrometry (LC-ESI-MS) in the presence of at least one labeled reference influenza HA peptide, to quantify the amount of immunogenic influenza HA in the sample;

wherein immunogenic influenza HA is associated with influenza HA in a pre-fusion state and inactive influenza HA is associated with influenza HA in a post-fusion state.

3. The method of claim 1, wherein the biological proteolysis comprises proteolysis with a protease.

4. The method of claim 3, wherein the protease is a serine protease.

5. The method of claim 1, wherein the step of separating the immunogenic influenza HA comprises protein precipitation.

6. The method of claim 5, wherein the protein precipitation comprises a step of adding an organic solvent.

7. The method of claim 6, wherein the organic solvent is acetone, ethanol or methanol.

8. The method of claim 5, wherein the method comprises a step of washing the precipitated protein with an alcohol.

9. The method of claim 1, wherein the sample is selected from the group consisting of: a whole virion influenza vaccine, a split influenza vaccine, a subunit influenza vaccine, and a recombinant influenza vaccine.

10. The method of claim 9, wherein the sample comprises an adjuvant.

11. The method of claim 1, wherein the LC-ESI-MS is Isotope Dilution Mass Spectrometry (IDMS).

12. The method of claim 1, wherein the labeled reference influenza HA peptide comprises an isotope label.

13. A method for manufacturing an influenza vaccine, the method comprising steps of:

a) providing a sample from a bulk preparation comprising the influenza HA of claim 1, b) quantifying the amount of immunogenic influenza HA according to the method of claim 1, and c) packaging unit dosage forms from the bulk preparation according to the amount of immunogenic influenza HA in the sample.

14. A method for preparing an influenza vaccine, comprising the steps of:

a) quantifying the amount of influenza HA in a bulk vaccine by the method of claim 1; and b) preparing a vaccine from the bulk.

15. The method of claim 2, wherein the sample is selected from the group consisting of: a whole virion influenza vaccine, a split influenza vaccine, a subunit influenza vaccine, and a recombinant influenza vaccine.

16. The method of claim 15, wherein the sample comprises an adjuvant.

17. The method of claim 2, wherein the LC-ESI-MS is Isotope Dilution Mass Spectrometry (IDMS).

18. The method of claim 2, wherein the labeled reference influenza HA peptide comprises an isotope label.

19. A method for manufacturing an influenza vaccine, the method comprising steps of:
    a) providing a sample from a bulk preparation comprising the influenza HA of claim 2,
    b) quantifying the amount of immunogenic influenza HA according to the method of claim 2, and
    c) packaging unit dosage forms from the bulk preparation according to the amount of immunogenic influenza HA in the sample.

20. A method for preparing an influenza vaccine, comprising the steps of:
    a) quantifying the amount of influenza HA in a bulk vaccine by the method of claim 2; and
    b) preparing a vaccine from the bulk.

21. The method of claim 8, wherein the alcohol is ethanol.

22. The method of claim 10, wherein the adjuvant is an oil-in-water emulsion adjuvant.

23. The method of claim 16, wherein the adjuvant is an oil-in-water emulsion adjuvant.

24. The method of claim 12, wherein the isotope label is selected from the list consisting of $^{15}N$ and $^{13}C$.

25. The method of claim 18, wherein the isotope label is selected from the list consisting of $^{15}N$ and $^{13}C$.

26. The method of claim 4, wherein the serine protease is trypsin.

* * * * *